(12) United States Patent
Mattsson et al.

(10) Patent No.: US 9,518,987 B2
(45) Date of Patent: *Dec. 13, 2016

(54) PROSTATE KALLIKREIN ALLERGEN

(71) Applicant: Phadia AB, Uppsala (SE)

(72) Inventors: Lars Mattsson, Uppsala (SE); Jonas Lidholm, Knivsta (SE); Henrik Everberg, Stockholm (SE)

(73) Assignee: PHADIA AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/930,737

(22) Filed: Nov. 3, 2015

(65) Prior Publication Data

US 2016/0051666 A1 Feb. 25, 2016

Related U.S. Application Data

(63) Continuation of application No. 14/276,861, filed on May 13, 2014, now Pat. No. 9,274,114, which is a continuation of application No. 12/520,243, filed as application No. PCT/SE2007/051080 on Dec. 21, 2007, now Pat. No. 9,182,400.

(60) Provisional application No. 60/876,958, filed on Dec. 22, 2006.

(30) Foreign Application Priority Data

Dec. 22, 2006 (SE) ...................... 0602804

(51) Int. Cl.
| | | |
|---|---|---|
| *A61K 39/00* | (2006.01) | |
| *A61K 38/00* | (2006.01) | |
| *A61K 39/395* | (2006.01) | |
| *C07K 1/00* | (2006.01) | |
| *C07K 2/00* | (2006.01) | |
| *C07K 4/00* | (2006.01) | |
| *C07K 5/00* | (2006.01) | |
| *C07K 7/00* | (2006.01) | |
| *C07K 14/00* | (2006.01) | |
| *C07K 16/00* | (2006.01) | |
| *C07K 17/00* | (2006.01) | |
| *G01N 33/53* | (2006.01) | |
| *G01N 33/573* | (2006.01) | |
| *A61K 39/35* | (2006.01) | |
| *C07K 16/18* | (2006.01) | |
| *G01N 33/68* | (2006.01) | |

(52) U.S. Cl.
CPC ............ *G01N 33/573* (2013.01); *A61K 39/35* (2013.01); *C07K 16/18* (2013.01); *G01N 33/6854* (2013.01); *G01N 2333/47* (2013.01); *G01N 2333/96455* (2013.01)

(58) Field of Classification Search
None
See application file for complete search history.

(56) References Cited

U.S. PATENT DOCUMENTS

| 5,667,979 A | 9/1997 | Berrens |
| 6,235,486 B1 * | 5/2001 | Young ................. C12Q 1/6886 |
| | | 435/330 |
| 9,182,400 B2 * | 11/2015 | Mattsson ............... A61K 39/35 |
| 2003/0216306 A1 | 11/2003 | Sabbadini et al. |
| 2003/0224462 A1 | 12/2003 | Parsons |

FOREIGN PATENT DOCUMENTS

| EP | 0 377 229 A1 | 7/1990 |
| WO | 01/61305 A2 | 8/2001 |
| WO | 2004/109291 A2 | 12/2004 |
| WO | 2005/075664 A1 | 8/2005 |
| WO | 2006/017538 A2 | 2/2006 |

OTHER PUBLICATIONS

Weidinger et al. 'Prostate-specific antigen as allergen in human seminal plasma allergy.' J. Allergy. Clin. Immunol. 117(1):213-215, 2006. Published online on Dec. 5, 2005.*
Taylor et al, "Respiratory Allergy to Urine Proteins of Rats and Mice," The Lancet, pp. 847-849, Oct. 22, 1977.
Ohman, Jr., "Allergy in Man Caused by Exposure to Mammals," Journal of the American Veterinary Medical Association, vol. 172, No. 12, pp. 1403-1406, Jun. 15, 1978.
Siraganian et al, "Characterization of Mouse Allergens," Journal of Allergy and Clinical Immunology, vol. 63, No. 6, pp. 435-442, Jun. 1979.
Schumacher, "Characterization of Allergens from Urine and Pelts of Laboratory Mice," Molecular Immunology, vol. 17, pp. 1087-1095, 1980.
Hoffman, "Dog and Cat Allergens: Urinary Proteins or Dander Proteins?" Annals of Allergy, vol. 45, pp. 205-206, Oct. 1980.
Boutin et al, "Allergenicity and Cross-Reactivity of Cat and Dog Allergenic Extracts," Clinical Allergy, vol. 18, pp. 287-293, 1988.
Chapdelaine et al, "Nucleotide Sequence of the Androgen-Dependent Arginine Esterase mRNA of Canine Prostate," FEBS Letters, vol. 232, No. 1, pp. 187-192, May 1988.
de Groot et al, "Affinity Purification of a Major and a Minor Allergen from Dog Extract: Serologic Activity of Affinity-Purified Can f 1 and of Can f I-Depleted Extract," Journal of Allergy and Clinical Immunology, vol. 87, No. 6, pp. 1056-1065, Jun. 1991.

(Continued)

*Primary Examiner* — Nora Rooney
(74) *Attorney, Agent, or Firm* — Porter Wright Morris & Arthur LLC

(57) ABSTRACT

Methods for treatment of a Type I allergy in a mammal comprise administering to an individual in need of such treatment a polypeptide of SEQ ID NO: 1 or the mature protein, amino acids 25-260, of the polypeptide of SEQ ID NO: 1, or a fragment of the polypeptide or the mature protein, which fragment shares epitopes for antibodies with the polypeptide or the mature protein, respectively, or a hypoallergenic form thereof that is modified to abrogate or attenuate its IgE binding response. Diagnostic kits comprise the polypeptide of SEQ ID NO: 1 or the mature protein, amino acids 25-260, of the polypeptide of SEQ ID NO: 1, immobilized on a solid support.

18 Claims, 14 Drawing Sheets

(56) References Cited

OTHER PUBLICATIONS

Spitzauer et al, "Characterisation of Dog Allergens by Means of Immunoblotting," International Archives of Allergy and Immunology, vol. 100, pp. 60-67, 1993.
Bayard et al, "Purification and Identification of Allergenic o2u-Globulin Species of Rat Urine," Biochimica et Biophysica Acta, vol. 1290, pp. 129-134, 1996.
Custovic et al, "Domestic Allergens in Public Places II: Dog (Can f 1) and Cockroach (Bla g 2) Allergens in Dust and Mite, Cat, Dog and Cockroach Allergens in the Air in Public Buildings," Clinical and Experimental Allergy, vol. 26, pp. 1246-1252, 1996.
Shevchenko et al, "Mass Spectrometric Sequencing of Proteins from Silver-Stained Polyacrylamide Gels," Analytical Chemistry, vol. 68, No. 5, pp. 850-858, Mar. 1, 1996.
Konieczny et al, "The Major Dog Allergens, Can fl and Can f2, are Salivary Lipocalin Proteins: Cloning and Immunological Characterization of the Recombinant Forms," Immunology, vol. 92, pp. 577-586, 1997.
Frenette et al, "Purification of Enzymatically Active Kallikrein hK2 from Human Seminal Plasma," Biochimica et Biophysica Acta, vol. 1334, pp. 109-115, 1997.
Spitzauer, "Allergy to Mammalian Proteins: At the Borderline Between Foreign and Self?" International Archives of Allergy and Immunology, vol. 120, pp. 259-269, 1999.
Valenta et al, The Recombinant Allergen-Based Concept of Component-Resolved Diagnostics and Immunotherapy(CRD and CRIT), Clinical and Experimental Allergy, vol. 29, pp. 896-904, 1999.
van Eijk et al, "Automated Isolation of High-Purity Plasma Albumin for Isotope Ratio Measurements," Journal of Chromatography B, vol. 731, pp. 199-205, 1999.
Cabanas et al, "Importance of Albumin in Cross-Reactivity Among Cat, Dog and Horse Allergens," Journal of Investigational Allergology and Clinical Immunology, vol. 10(2), pp. 71-77, Mar.-Apr. 2000.
DeWitt et al, "Molecular and Immunological Characterization of a Novel Timothy Grass (*Phleum pratense*) Pollen Allergen, Phl p. 11," Clinical and Experimental Allergy, vol. 32, pp. 1329-1340, 2002.
Hiller et al, "Microarrayed Allergen Molecules: Diagnostic Gatekeepers for Allergy Treatment," The FASEB Journal, vol. 16, pp. 414-416, Mar. 2002.
Demoly et al, "Allergy Series X: Progress in Diagnosis of Allergy In Vitro, Allergen-Induced Mediator Release Tests," Allergy, vol. 58, pp. 553-558, 2003.
Mahler et al, "Vaccines for Birch Pollen Allergy Based on Genetically Engineered Hypoallergenic Derivatives of the Major Birch Pollen Allergen, Bet v 1," Clinical and Experimental Allergy, vol. 34, pp. 115-122, 2004.

Ebo et al, "In Vitro Allergy Diagnosis: Should We Follow the Flow?" Clinical and Experimental Allergy, vol. 34, pp. 332-339, 2004.
Saarelainen et al, "Assessment of Recombinant Dog Allergens Can f 1 and Can f 2 for the Diagnosis of Dog Allergy," Clinical and Experimental Allergy, vol. 34, pp. 1576-1582, 2004.
Weidinger et al, "IgE-Mediated Allergy Against Human Seminal Plasma," Chemical Immunology Allergy, vol. 88, pp. 128-138, 2005.
Gafvelin etal, "Cytokine and Antibody Responses in Birch-Pollen-Allergic Patients Treated with Genetically Modified Derivatives of the Major Birch Pollen Allergen Bet v 1," International Archives of Allergy and Immunology, vol. 138, pp. 59-6, 2005 (online Aug. 11, 2005).
Jutel et al, "Allergen-Specific Immunotherapy with Recombinant Grass Pollen Allergens," Journal of Allergy and Clinical Immunology, vol. 116, No. 3, pp. 608-613, Sep. 2005.
Cromwell et al, "Strategies for Recombinant Allergen Vaccines and Fruitful Results from First Clinical Studies," Immunology and Allergy Clinics of North America, vol. 26, pp. 261-281, 2006.
ImmunoCAP is it Allergy?, Phadia AB Brochure, Russian and English versions, Undated.
UniCAP Specific IgE, Latex Allergen ImmunoCAP k82 510(k) Submission, pp. 1 and 67-70, Pharmacia & Upjohn, and FDA Review Letter (1997).
Baumgarten et al, Concentrations of Glandular Kallifrein in Human Nasal Secretions Increase During Experimentally Induced Allergic Rhinitis, The Journal of Immunology, vol. 137, No. 4, p. 1323-1328 (1986).
Christiansen et al, Detection of Tissue Kallikrein in the Bronchoalveolar Lavage Fluid of Asthmatic Subjects, J. Clin Invest, The American Society for Clinical Investigation, vol. 79, p. 188-197 (1987).
Yousef et al, An overview of the kallikrein gene families in humans and other species: Emerging candidate tumour markers, Clin. Biochem., 36:443-452 (2003).
Lerner et al, Tapping the immunological repertoire to produce antibodies of predetermined specificity, Nature, 299:592-596 (1982).
Berrens L: "An IgE-binding TAME esterase in the urine of the mouse, *Mus musculus domesticus*" Immunology Letters, vol. 47, No. 1-2, 1995, pp. 29-32.
Kim et al, Protein immobilization techniques for microfluidic assays, Biomicrofluidics 7, 041501, 2013.
Goel et al, http://www.rpi.edu/dept/chem-eng/Biotech-Environ/IM-MOB/goel2nd.html., 1994.
Official Action dated Oct. 30, 2015, from corresponding Canadian Application No. 2,673,366.
Bell et al., Evaluation of Serum and Seminal Plasma Markers in the Diagnosis of Canine Prostatic Disorders, Journal of Veterinary Internal Medicine, vol. 9, No. 3:149-153 (May-Jun. 1995).

* cited by examiner

PROSTATE KALLIKREIN ALLERGEN

The Sequence Listing entitled 173400B-November-2-2015-ST25.txt created Nov. 2, 2015 having a size of 4792 bytes is incorporated by reference.

FIELD OF THE INVENTION

The present invention relates to the field of allergy. More specifically, the invention relates to the identification of novel allergens from mammals and to diagnosis and treatment of allergy towards mammals.

BACKGROUND

Dog dander is a common cause of indoor allergy with symptoms including rhinitis, conjunctivitis, bronchial inflammation and asthma. Dog allergens can be detected not only in houses where dogs are kept as pets but also in other places such as schools and day care centres where dogs are not present on a regular basis (1).

Allergy to dog is accompanied and dependent of sensitization to proteins released from dog hairs and dander. In cases of suspected allergy to dog, the clinical investigation includes assessment of sensitization by skin prick or specific IgE antibody measurement using extract of dog hair and/or dander. A laboratory immunoassay for specific IgE, such as a Phadia ImmunoCAP, can detect most cases of sensitization to dog using natural dog dander extract due to favourable assay conditions and a large solid phase available for allergen attachment.

Dog hair and dander extracts contain a complexity of allergenic and non-allergenic proteins (2, 3). Three dog allergens have so far been identified and studied in detail: Can f 1, Can f 2 and Can f 3. Can f 1, a member of the lipocalin protein family, with reported molecular weight of 21-25 kD, was first purified by de Groot et al. (4) and later cloned and expressed as a recombinant protein (5). Can f 2 belongs to the same protein family but is a protein distinct from Can f 1 (4, 5). Can f 3, dog serum albumin, is a relatively conserved protein demonstrating extensive cross-reactivity to other mammalian albumins (6).

Of the known dog allergens, Can f 1 is the most important, binding IgE antibodies from approximately half of dog allergic subjects (7). About 20% of dog allergic subjects display IgE binding to Can f 2 but most of these are also sensitized to Can f 1. Although 30-40% of adult dog allergic individuals may show IgE binding to Can f 3 (2, 8), the specific clinical relevance of mammalian serum albumins is uncertain.

It has been known for a long time that major allergens relevant to allergy to rodents, such as mice and rats, are present in the animals' urine and these have been isolated and extensively characterized (9-13). IgE antibody binding activity has also been reported to exist in urine of other animals, including cats and dogs (14), but no allergen has been purified from urine of these animals and characterized at a molecular level.

SUMMARY OF THE INVENTION

As stated above, a laboratory immunoassay for specific IgE can detect most cases of sensitization to dog using natural dog dander extract due to favourable assay conditions and a large solid phase available for allergen attachment. However, in a miniaturized or non-laboratory immunoassay, such as an allergen microarray or a doctor's office test, the combination of less favourable assay conditions, lower capacity for antibody-binding allergen reagent and natural allergen extract of limited potency, has been found to cause insufficient diagnostic sensitivity. A similar situation may exist also for immunoassays for specific IgE to other animal epithelia. Thus, there is a need in some cases to use pure allergenic proteins to achieve sufficient sensitivity in diagnostic tests for specific IgE.

Furthermore, a significant proportion of dog allergic individuals also do not react to any of the known identified dog allergens and this was recently demonstrated in a Finnish population (7).

The above led the present inventors to look for additional, not yet identified, dog allergens. Such novel allergens may be useful not only as reagents for increased sensitivity in routine diagnostic tests, but also as a complement to known dog allergens in different types of component-resolved diagnostic applications (15, 16). Pure allergenic proteins, or fragments and variants thereof with improved non-anaphylactic properties, may also be used in component-resolved immunotherapy (16-20).

A new major allergen has thus been purified from dog urine and identified as prostatic kallikrein. It is in all aspects distinct from previously known dog allergens. Further, a similar or identical and immunologically equivalent allergen has been found to exist in dog dander extract. Kallikrein represents an important addition to the panel of known dog allergens and will be useful in the diagnosis of dog allergy. It is also anticipated that homologous proteins from other mammals, such as cat, horse and rodents, including rat and mouse, will have similar allergenic properties and diagnostic utility.

Prostatic kallikrein was found to exist not only in urine but also in the fur of dander of dogs. However, the fact that protein specifically expressed in prostate tissue would be restricted to male individuals, suggests that female dogs would lack this allergen. Preliminary results in our laboratory indeed support this notion and, if corroborated by results from more extensive studies, the implication would be that dog allergic individuals sensitized exclusively to prostatic kallikrein may tolerate female dogs.

In a recently published report, it was demonstrated that vaginal hypersensitivity reaction to ejaculate was associated with IgE sensitization to human prostate-specific antigen, PSA, present in seminal plasma (21). As canine and human prostatic kallikrein and human prostate-specific antigen have partial sequence similarity, it is possible that sensitization to canine prostate-specific kallikrein confers an elevated risk of developing such allergic reactions. It can also be envisaged that IgE-mediated immune reactions to prostate-specific kallikrein may play a role in certain cases of infertility in humans.

In one aspect the invention relates to the use of kallikrein in diagnosis of Type I allergy and the use of kallikrein for the manufacture of a composition for diagnosis of Type I allergy.

In a further aspect the invention relates to an allergen composition "spiked" with kallikrein. Such an allergen composition may be an allergen extract or a mixture of purified or recombinant allergen components having no or a low kallikrein content, wherein the kallikrein is added in order to bind IgE from patients whose IgE would not bind or bind poorly to the other allergen components in the composition. This aspect of the invention also relates to a method for producing such a composition, which method comprises the step of adding kallikrein to an allergen composition, such as an allergen extract (optionally spiked with other components) or a mixture of purified native or recombinant allergen components.

In yet a further aspect the invention relates to an in vitro diagnostic method for diagnosing a Type I allergy in a patient, wherein a body fluid sample such as a blood or serum sample from the patient is brought into contact with kallikrein or a composition according to the previous aspect, and it is detected whether or not the patient sample contain IgE antibodies that bind specifically to kallikrein. Such a diagnostic method may be carried out in any manner known in the art. The kallikrein may e.g. be immobilized on a solid support, such as in a conventional laboratory immunoassay, in a microarray or in a lateral flow assay.

In a further aspect the invention relates to a diagnostic kit for performing the method according to the previous aspect, which kit includes kallikrein.

In the above mentioned aspects, the wildtype kallikrein molecule may be replaced with fragments or variants of kallikrein, natural or man-made, sharing epitopes for antibodies with wildtype kallikrein, as defined below.

The invention further relates to a method of treatment of Type I allergy comprising administering to a patient in need of such treatment a kallikrein or a modified kallikrein, as explained below. This aspect of the invention also relates to the use of kallikrein in such immunotherapy, including e.g. component-resolved immunotherapy (16). In one embodiment of this aspect, the kallikrein may be used in its natural form or in a recombinant form displaying biochemical and immunological properties similar to those of the natural molecule. In another embodiment, kallikrein may be used in a modified form, generated chemically or genetically, in order to abrogate or attenuate its IgE antibody binding capacity, while preferably being capable of eliciting an IgG response in a treated individual. Examples of modifications include, but are not limited to, fragmentation, truncation or tandemerization of the molecule, deletion of internal segment(s), substitution of amino acid residue(s), domain rearrangement, or disruption at least in part of the tertiary structure by disruption of disulfide bridges or it's binding to another macromolecular structure, or by removal of the protein's ability to bind calcium ions or other low molecular weight compounds. In yet another embodiment of this aspect, the individual 10 kDa and/or the 18 kDa subunits of kallikrein, which display reduced IgE binding activity as compared to the intact molecule, are used as modified kallikrein.

In all of the above mentioned aspects of the invention, the kallikrein can be derived from any mammal producing kallikrein capable of inducing an allergic response in a patient. The kallikrein may be purified from its natural source, such as from urine, saliva or other body fluids, or from tissue, such as hair or dander, of the mammal in question. It may also be produced by recombinant DNA technology or chemically synthesized by methods known to a person skilled in the art.

The invention also relates to canine prostatic kallikrein for use in diagnosis and therapy, such as diagnosis and therapy of Type I allergy to dog.

The invention also relates to a method for purification of kallikrein from mammalian urine, comprising the steps
filtering the mammalian urine;
buffer exchange with a buffer suitable for hydrophobic interaction chromatography;
filtering of the buffer exchanged urine sample;
applying the buffer exchanged urine sample to a hydrophobic interaction chromatography column; and
collecting the flow-through fraction comprising kallikrein.

The mammalian urine may be canine urine.

DEFINITIONS

Kallikreins are proteolytic enzymes from the serine endopeptidase family found in normal blood and urine. In the IUBMB enzyme nomenclature system, plasma kallikrein has been assigned number EC 3.4.21.34 and tissue kallikrein number EC 3.4.21.35. Urinary kallikrein from dog is a 28 kDa heterodimeric protein comprising two subunits of approximately 10±2 and 18±2 kDa, respectively, for the purposes of this invention referred to as the 10 and 18 kDa subunits, respectively. It has an amino acid sequence according to SEQ ID NO: 1, GenBank Accession no: P09582, and homologous proteins have been described in a wide range of mammalian species, including, horse, cow, pig, mouse, rat and primates (e.g. Accession no AAQ23713-4 (horse), NP_001008416 (cow), P00752 (pig), P00755-6 and P15947 (mouse), P36373 and P00758 (rat), Q28773 (baboon), XP_001174026 (chimpanzee), Q07276 (macaque), P20151, Q07276 and AAM11874 (human).

Variants and fragments of a kallikrein should be construed as meaning proteins or peptides with a length of at least 10 amino acids, more preferably at least 50, even more preferably at least 75 or 100 amino acid residues, and a sequence identity to said kallikrein of at least 50%, preferably over 60%, 70%, 80%, 90% or 95%.

A modified kallikrein should in the context of the present invention be construed as meaning a kallikrein that has been chemically or genetically modified to change its immunological properties, e.g. as exemplified above in relation to the immunotherapy aspect of the invention.

Variants and fragments of kallikrein sharing epitopes for antibodies with wildtype kallikrein should be construed as being those fragments and variants whose binding of IgE antibodies from a serum sample from a representative kallikrein sensitized patient can be significantly inhibited by kallikrein. Such an inhibition assay may e.g. be performed according to the protocol disclosed in Example 8.

A hypoallergenic modified kallikrein or variant or fragment of kallikrein should be construed as being a modified kallikrein or variant or fragment of kallikrein that is not capable of binding kallikrein reactive IgE antibodies from a serum sample of a representative kallikrein sensitized patient, as determined e.g. by the protocol according to Example 3 or which displays no or significantly reduced biological allergen activity, as determined by a cellular activation assay such as the basophil histamine release assay (22, 23).

DETAILED DESCRIPTION OF THE INVENTION

The examples below illustrate the present invention with the isolation and use of kallikrein from dog. The examples are only illustrative and should not be considered as limiting the invention, which is defined by the scope of the appended claims.

Example 1

Detection and Isolation of an IgE Binding Protein from Dog Urine

Figure 1:
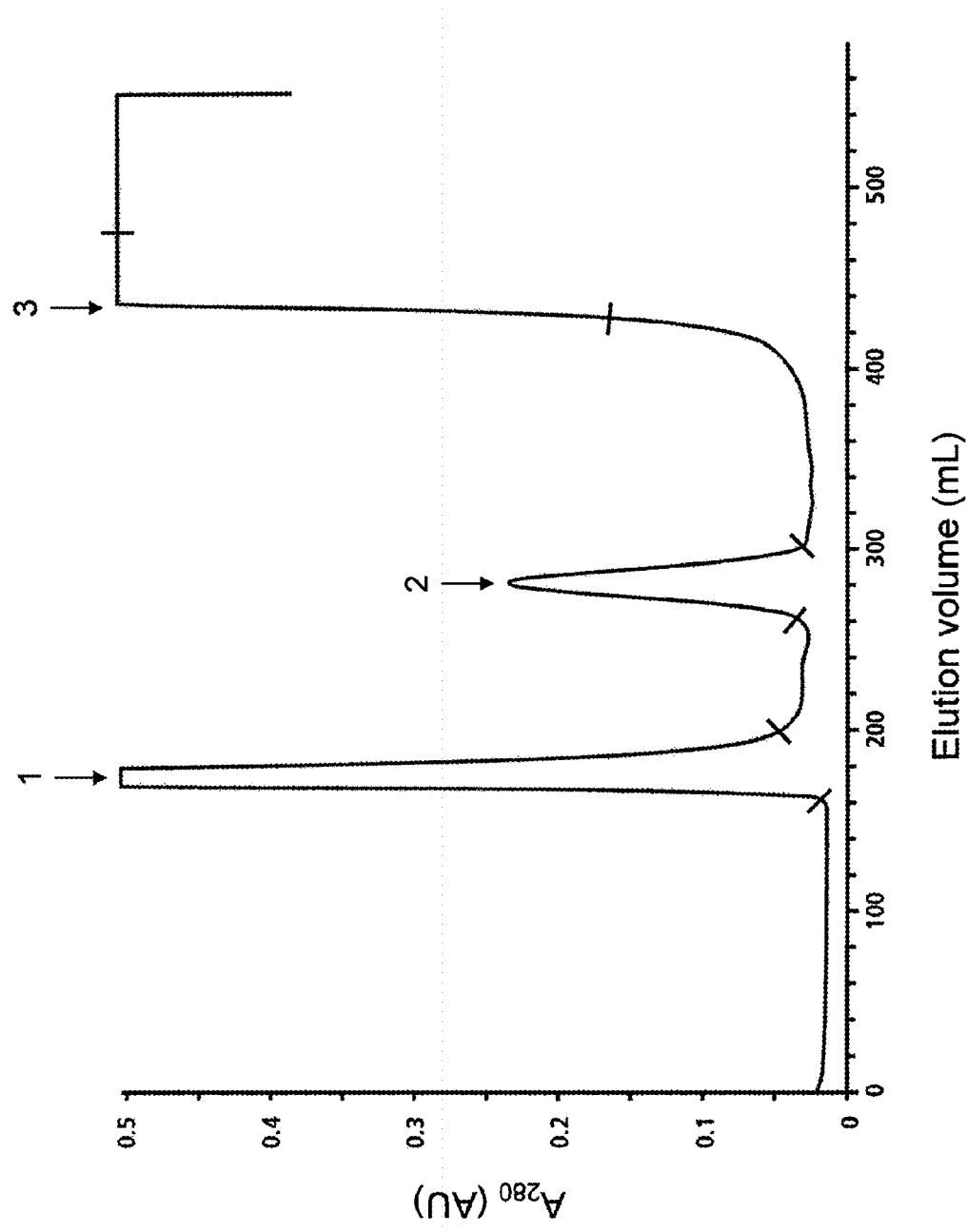
FIG. 1 shows the fractionation of dog urinary proteins by size exclusion chromatography. Fractions comprising each of the three peaks indicated in the figure (labeled 1-3) were pooled as indicated for analysis of IgE binding activity.

In order to investigate whether dog urine may contain allergens relevant to dog allergy in humans, the following experiments were performed. Urine was collected from a 7 year old male crossbreed between Siberian Husky and Vorsteh. After filtration through a 0.45 μm mixed cellulose ester filter, 10 mL of urine was applied to a Superdex 75 size exclusion chromatography (SEC) column (XK26/100, $V_t$=505 mL, GE Healthcare Biosciences, Uppsala, Sweden) equilibrated with 20 mM MOPS pH 7.6, 0.5 M NaCl (MBS) and elution was performed with the same buffer at a flow rate of 2 mL/min. Fractions from three peaks were pooled as indicated in the chromatogram shown in FIG. 1 and analysed for allergen activity. The protein content of each fraction was immobilized on ImmunoCAP (Phadia, Uppsala, Sweden) solid phase and its IgE antibody binding activity tested using eight sera from dog dander sensitized individuals. Most of these sera were selected as having high IgE binding to dog dander extract but relatively low binding to rCan f 1, rCan f 2 and nCan f 3. Of the three peaks tested, peak 2 was found to contain by far the highest level of IgE binding activity (Table 1). Sodium dodecyl sulfate polyacrylamide gel electrophoresis (SDS-PAGE) using the NuPAGE MES buffer system (10% NuPAGE gel, Invitrogen, Carlsbad, Calif., USA) of a reduced sample of peak 2 revealed two dominant protein bands, with apparent molecular weights of approximately 10 and 18 kDa, respectively (not shown).

Figure 2:
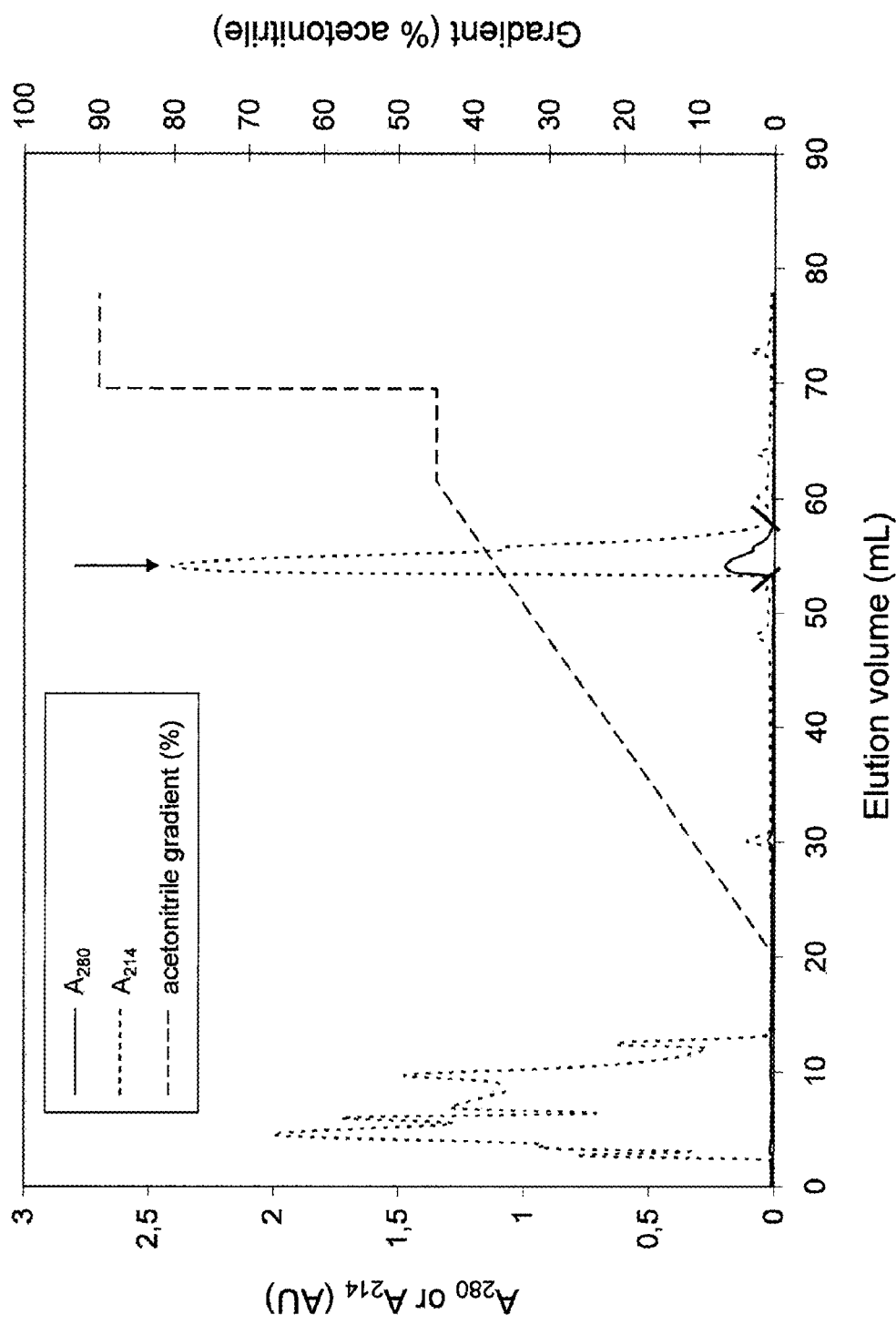
FIG. 2 shows the purification of an IgE binding protein from peak 2 of FIG. 1 by reversed phase chromatography. The peak containing the protein selected for further investigation is indicated by an arrow.
Figure 3:
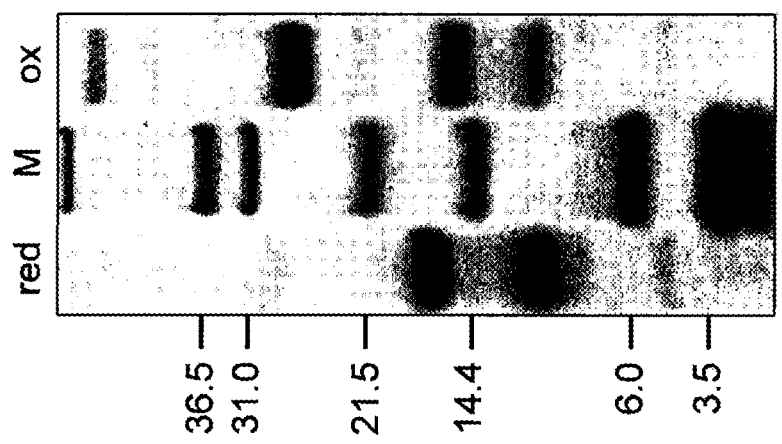
FIG. 3 is an SDS-PAGE analysis of reduced (red) and non-reduced (ox) samples of the IgE binding protein purified from dog urine by size exclusion and reversed phase chromatography. Lane M contains molecular weight marker proteins.

Further protein purification from the pool corresponding to peak 2 was performed using a Source 15 reversed phase chromatography (RPC) column (ST4.6/100, $V_t$=1.66 mL, GE Healthcare Biosciences). After addition of trifluoro acetic acid (TFA) to a final concentration of 0.065%, the pool was applied to the column, followed by washing with 9 column volumes of 0.065% TFA in water. Elution was performed with a 0-45% linear gradient of acetonitrile in water containing 0.05% TFA, resulting in one distinctive but somewhat asymmetrical peak (FIG. 2, peak indicated by an arrow). SDS-PAGE of reduced samples of fractions containing this peak revealed the presence of both the 10 and 18 kDa bands, seemingly unseparable (FIG. 3). The fractions covering the entire peak were therefore pooled as indicated by horizontal bars in FIG. 2. SDS-PAGE of a non-reduced sample of this pool revealed an additional band of 28 kD and a slight shift in mobility of the 10 kDa and 18 kDa bands (FIG. 3). A faint protein band of approximately 55 kDa can also be seen in the non-reduced state, which may be a dimer of the 28 kDa protein. The occurrence of the 28 kDa band in the non-reduced state suggested that this protein may be made up of the 10 and 18 kDa polypeptides, joined together by one or more cystein bridge(s). The fact that linear mass spectromemetric analysis (data not shown) later showed dissociation of the 28 kDa component upon reduction and alkylation added further evidence to this notion.

Example 2

Identification of the IgE Binding Protein from Dog Urine as Prostate Kallikrein

Mass spectrometry and N-terminal sequencing was used to determine the identity of the IgE binding protein isolated from dog urine.

Peptide Mass Fingerprint Analysis by MALDI-TOF

For in-solution digestion of the RPC purified urinary protein, reduction and alkylation was performed by sequentially adding to the sample DTT and iodoacetamide at approximately 45- and 100-fold molar excess, respectively. Trypsin digestion was then performed overnight at 37° C., using porcine trypsin (Trypsin Gold, mass spectrometry grade, Promega, Madison, Wis., USA). Samples containing digested peptides were spotted onto the MALDI target plate and α-cyano matrix in 50% acetonitrile, 10 mM $NH_4$ $[H_2PO_4]$, 0.1% TFA, was added. Following evaporation of the solvent, peptide mass fingerprinting (PMF) was performed in a Bruker Daltonics Autoflex 2 instrument (Bruker Daltonics, Bremen, Germany). To identify proteins matching PMF results obtained, the MSDB database was searched using a Mascot server (Matrixscience, London, UK). Post source decay (PSD) analysis was performed on selected peptides. External calibration was performed using a peptide calibration standard (Bruker Daltonics). In-gel digestion analysis of the individual protein bands from SDS-PAGE was performed essentially according to Shevchenko (24). In summary, the 10, 18 and 28 kDa bands described in Example 1 above were excised from a Coomassie brilliant blue stained SDS-PAGE gel. The gel pieces were sequentially washed with 50 mM ammonium bicarbonate containing 50% acetonitrile followed by shrinking in pure acetonitrile. After rehydration of the gel piece with 50 mM ammonium bicarbonate, acetonitrile was added to 50% and following a second acetonitrile wash step, the gel pieces were dried in a vacuum centrifuge. Eduction and alkylation was performed in sequence using 45 mM DTT and 100 mM iodoacetamide in 50 mM ammonium bicarbonate. After repeated washes with 50% acetonitrile in 50 mM ammonium bicarbonate and a final 100% acetonitrile wash, the gel particles were again dried down in a vacuum centrifuge. Trypsin digestion was performed overnight at 37° C. using porcine trypsin as described above. The digested sample was then sonicated and peptides extracted from the gel particles in 50% acetonitrile containing 0.1% TFA. Sample preparation and peptide mass fingerprinting was performed as described above. The PMF analysis of the in-solution digested urinary protein resulted in a highly significant match ($p<0.05$) to prostatic kallikrein from dog (Accession no P09582). PSD analysis of two peptides, m/z=1224.6 and m/z=1632.8, which were also present in the in-gel digestion analysis of the 18 kDa band, gave significant database matches to the amino acid sequences FMLCAGVLEGK (SEQ ID NO: 2) and SHDLMLLHLEEPAK (SEQ ID NO: 3), corresponding to residues 194-204 and 117-130, respectively, of the same protein database entry.

Corroborating results were obtained from analysis of the in-gel digested protein bands as PMF of the 28 kDa band also yielded a highly significant database match ($p<0.05$) to kallikrein from dog (P09582). Further evidence to the identity of the isolated urinary protein came from the analysis of in-gel digested samples of the 10 kDa band. PSD analysis of peptide m/z=1004.6 gave a highly significant ($p<0.05$) database match with the amino acid sequence SFIHPLYK (SEQ ID NO: 4), corresponding to residues 95-102 of P09582.

N-Terminal Amino Acid Sequencing

For N-terminal sequencing, the reduced 10 kDa and 18 kDa protein bands were excised separately from a SDS-PAGE gel and extracted in 6 M guanidinium-HCl, 20 mM Tris pH 8.0, 0.5 M NaCl, using a plastic rod for homogenization. N-terminal sequence analysis of the extracted 10 kDa and 18 kDa bands, performed using a Hewlett-Packard G1000A instrument (Hewlett-Packard, Palo Alto, Calif.), yielded the amino acid sequences IIGREXLKN (SEQ ID NO: 5) and AVIRPGEDRS (SEQ ID NO: 6), respectively, which were found to match residues 25-34 and 108-117 in the dog prostatic kallikrein precursor sequence of Accession no P09582.

Taken together, the results described in this example demonstrate that the major constituent of the purified dog urinary protein, corresponding to the 10 and 18 kDa bands in reducing SDS-PAGE analysis, is identical to prostatic kallikrein from dog. Further, the observations suggest that the 10 and 18 kDa polypeptides are formed by posttranslational cleavage of a primary gene product and are held together by disulfide bridges to form the 28 kDa protein seen under non-reducing conditions, similar to what has previously been described for human kallikrein (25).

Prostatic kallikrein is also known as arginine esterase and carries that designation in database entries describing identical or nearly identical amino acid sequences, including NP_001003284, CAA68720 and AAA30831. Further, we note that another variant of kallikrein, expressed in renal, pancreatic and salivary gland tissues, has been identified in dog (Accession No CAA53210) and shares 68% amino acid identity with prostatic kallikrein.

Example 3

Assessment of IgE Binding Activity of Kallikrein, rCan f 1, rCan f 2 and rCan f 3

In vitro IgE binding activity of the purified recombinant and natural dog allergens were examined using ImmunoCAP® (Phadia, Uppsala, Sweden), an immunoassay system used for specific IgE antibody measurement in clinical diagnosis of atopic allergy. Recombinant Can f 1 and Can f 2 (5) were cloned and expressed in *E. coli* essentially as described (26). Dog albumin was purified from serum using anion exchange chromatography and Blue Sepharose affinity chromatography, essentially as described (27). Experimental ImmunoCAP tests were prepared and used for serum analysis as described (26).

Sera from 37 dog allergic patients from Sweden (n=9), Spain (n=23) and North America (n=4) were used in the study. All patients had a positive skin prick test for dog dander extract and a doctors' diagnosis of dog allergy with symptoms of asthma, rhinoconjunctivitis and/or urticaria. All of the sera had a positive specific IgE test (ImmunoCAP) to dog dander extract.

The levels of specific IgE to dog dander extract, rCan f 1, rCan f 2, nCan f 3 and purified kallikrein are shown in Table 2 and a summary of the results is shown in Table 3. Of the tested sera, 29 showed IgE reactivity to kallikrein and 18 to rCan f 1. Both rCan f 2 and nCan f 3 appeared as minor allergens among the subjects studied, binding IgE from only 8 and 6 of 37, respectively. Fourteen of the 37 sera (38%) reacted only to kallikrein. On average among the kallikrein-reactive sera, the level of IgE binding to kallikrein amounted to 64% of the IgE binding to dog dander. The corresponding relative levels of IgE binding to rCan f 1, rCan f 2 and nCan f 3 were 45%, 25% and 47%, respectively, among sera specifically reactive to those allergens. Only two of the 37 sera tested lacked IgE reactivity to all of the four dog allergens. The IgE binding to kallikrein showed no correlation to any of the other dog allergens, demonstrating that the immune response to kallikrein is an independent variable and not a result of cross reactivity to Can f 1, Can f 2 or Can f 3.

The results obtained clearly demonstrated that prostatic kallikrein from dog is a major and unique allergen among the dog allergic subjects studied here. By both prevalence and magnitude of IgE binding, kallikrein was found to be the most important dog allergen so far described and among the subjects studied, over one third reacted to kallikrein but none of the other allergens tested.

Example 4

Demonstration of Kallikrein-Specific IgE Antibody Binding Activity in Dog Dander Extract An IgE inhibition experiment was performed to examine whether dog dander contains epitopes capable of binding kallikrein-reactive IgE antibodies. Serum samples from three dog sensitized subjects (A-C) with IgE reactivity to kallikrein were first incubated for 2 h at room temperature with purified kallikrein at a final concentration of 100 μg/mL and, in parallel as negative controls, with serum diluent or the non-allergenic maltose binding protein (MBP) of *E. coli*. All samples were then analysed in duplicate for IgE binding to ImmunoCAP tests carrying immobilized dog dander extract to study whether preincubation with kallikrein specifically would prevent IgE binding to dander protein attached to the solid phase. As a control for specificity of kallikrein as inhibitor, a serum from a subject (D) sensitized to Can f 1 and Can f 2, but not to kallikrein, was included alongside the other sera in the experiment.

Figure 4:
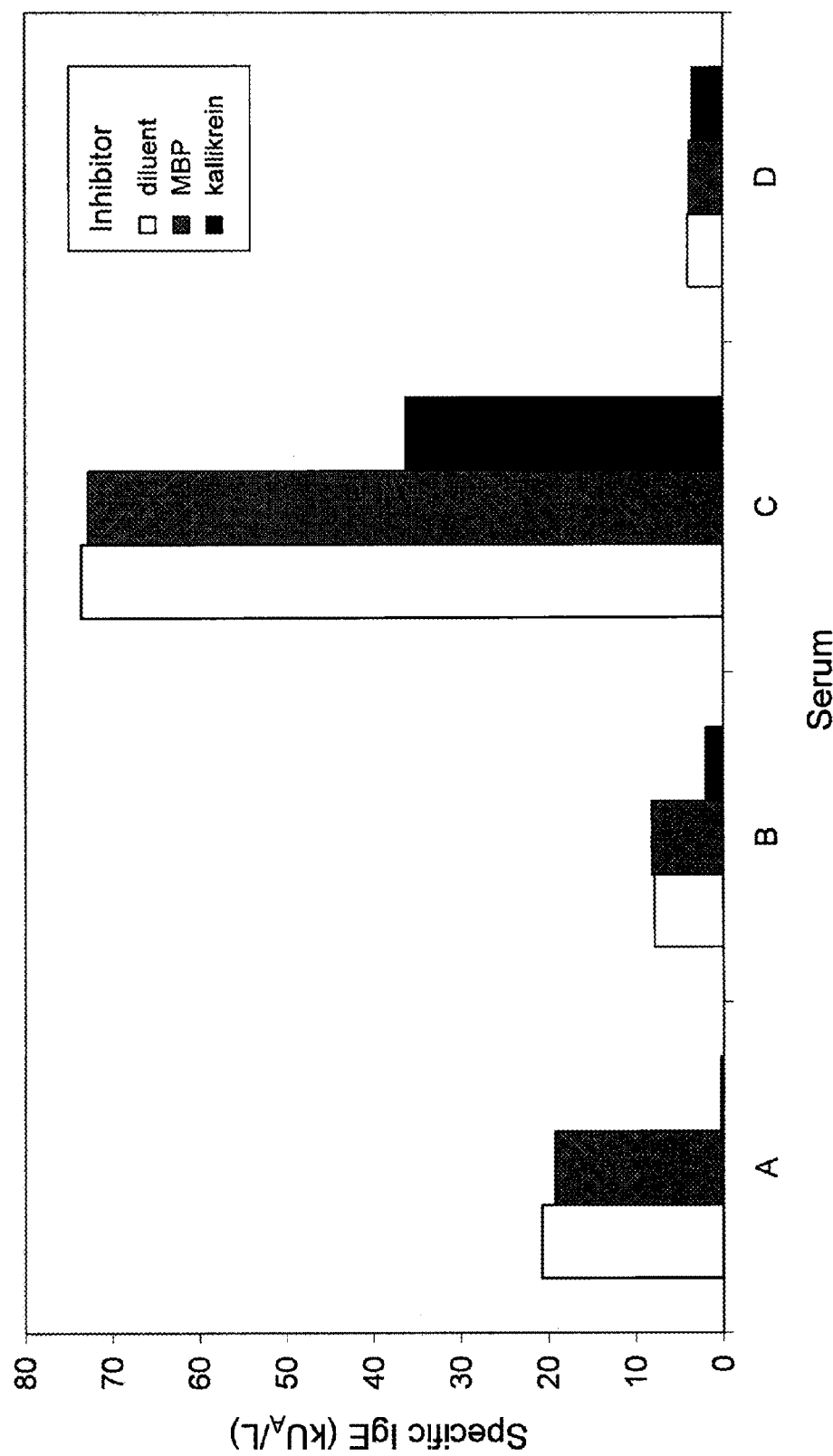
FIG. 4 shows the effect of kallikrein as a fluid-phase inhibitor on specific IgE binding to immobilized dog dander extract.

The results of the inhibition experiment are shown in FIG. 4. Kallikrein purified from dog urine was found to completely inhibit the IgE binding to dog dander of two (A and B) of the three kallikrein-reactive sera and partly the binding of the third serum (C), which was known to be reactive also to other dog allergens. The negative control protein, MBP, showed no significant inhibitory effect as compared to serum diluent. In addition, no inhibition by kallikrein was observed on IgE binding of the Can f 1- and Can f 2-reactive serum (D).

The results demonstrated that epitope structures capable of binding kallikrein-reactive IgE antibodies are present in dog dander and, hence, are not confined to urine.

Example 5

Assessment of IgE Binding to a Kallikrein-Like 28 kDa Protein from Dog Dander Extract Using Immunoblot Analysis With the aim to identify a protein present in dog dander to which the observed kallikrein-like allergen activity may be attributed, 37 sera with known levels of kallikrein-reactive IgE were used in an immunoblot experiment. Immunoblot analysis was performed on non-reduced dog dander extract separated by SDS-PAGE (12.5% Excel 2-D gel, GE Healthcare Biosciences) and electroblotted onto nitrocellulose membrane (Hybond ECL, GE Healthcare Biosciences). Protein blots were blocked for 1 h at room temperature using blocking buffer (50 mM phosphate pH 7.4, 0.1% (v/v) Tween-20, 0.9% (w/v) NaCl, 0.3% w/v) Dextran T10) and then incubated overnight with each patient's serum, diluted 1.5- to 20-fold in blocking buffer. The dilution factor for each serum is indicated in brackets at the top of its corresponding membrane strip in FIG. 5. After washing in blocking buffer with 0.5% (v/v) Tween-20, the membrane was incubated 4 hrs at room temperature with an $^{125}$I-labelled anti-human IgE antibody in blocking buffer and bound IgE was then radiographically detected using a storage phosphor screen and a Variable Mode Imager, Typhoon 9410 (GE Healthcare Biosciences).

Figure 5A:
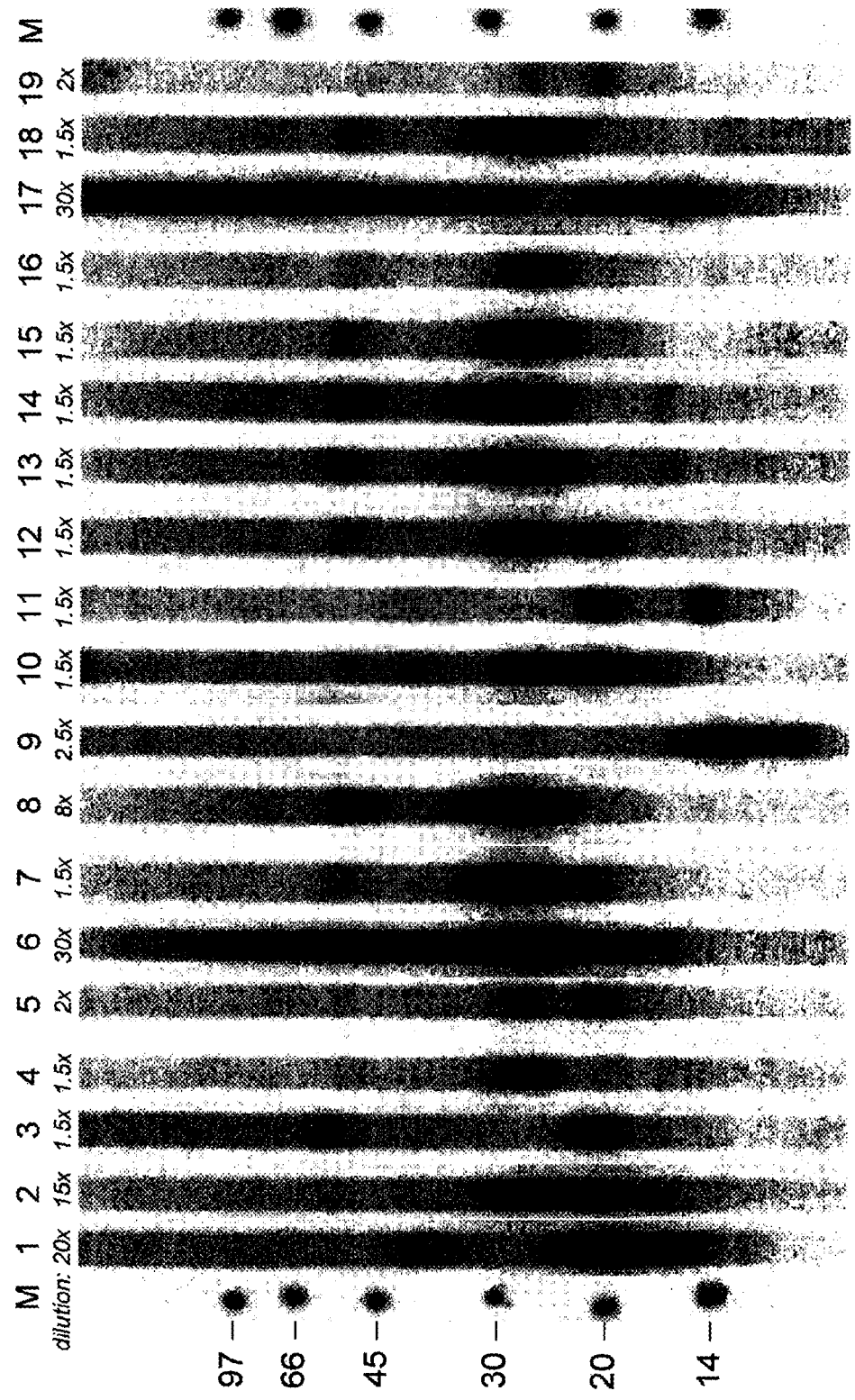
FIG. 5a-b is an assessment by immunoblot analysis of IgE antibody reactivity to dog dander extract in 37 dog allergic subjects' sera. Prior to incubation with the membrane strips, serum samples were diluted as indicated. Lane M contains molecular weight marker proteins.
Figure 5B:
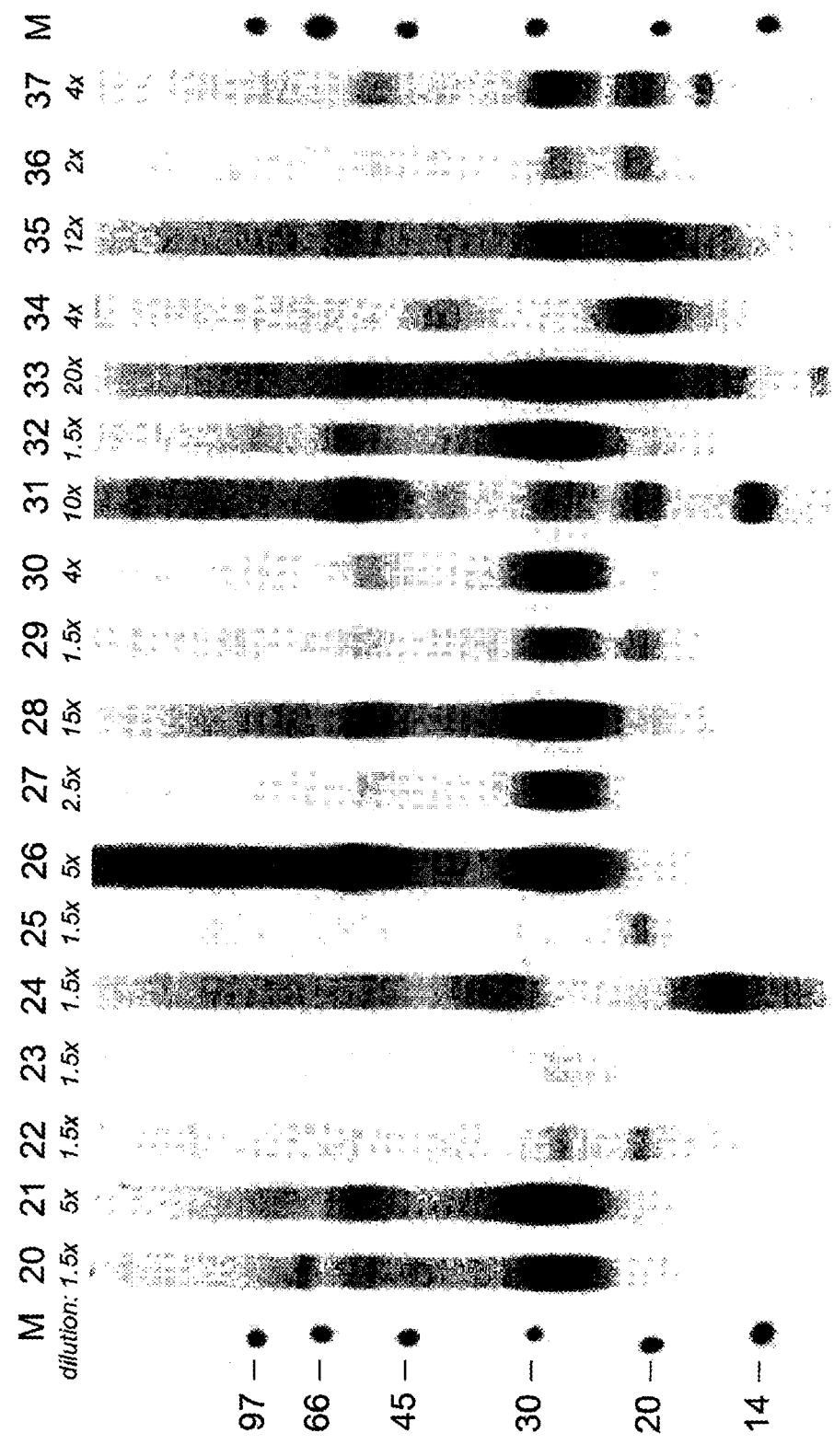
Figure 6:
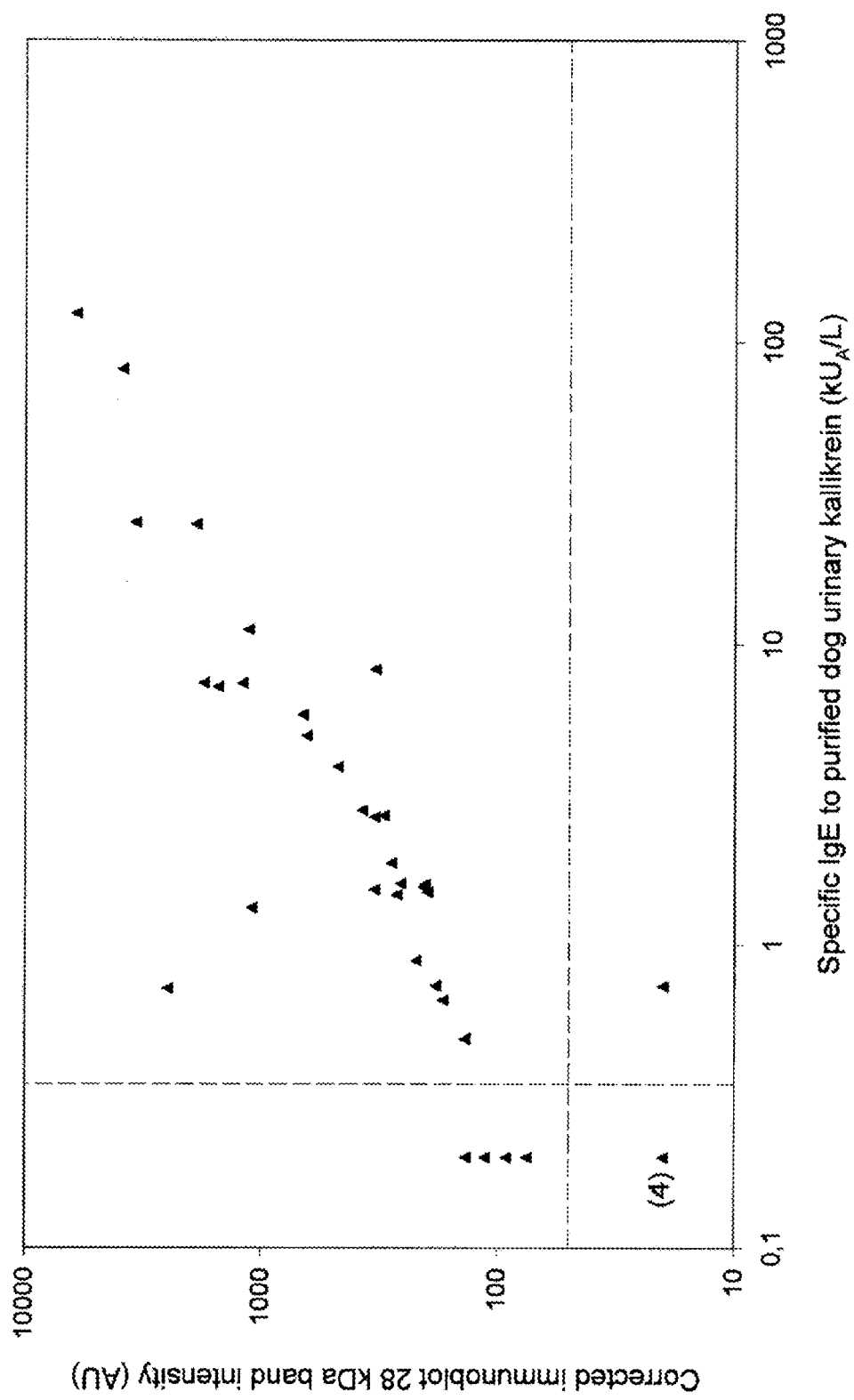
FIG. 6 shows a comparison of the immunoblot signal intensity of a 28 kDa band, corrected for serum dilution, and the level of kallikrein-specific IgE, as determined by experimental ImmunoCAP analysis. The ImmunoCAP and immunoblot detection limits applied are indicated by hatched lines. Immunoblot signal intensity is expressed in arbitrary units (AU).

The results of the experiment are shown in FIG. 5*a-b*. Of the 37 sera used, 30 showed IgE binding to a 28 kDa protein while 21 showed IgE binding to a 23 kDa band, corresponding to Can f 1 and/or possibly Can f 2. Immunoblotting signal intensities were quantified using the Phoretix 1D software (Nonlinear Dynamics Ltd, Newcastle upon Tyne, UK). The level of IgE reactivity in each serum to individual bands was calculated by multiplying the signal intensity with the serum dilution factor. FIG. 6 shows a comparison of the level of IgE binding to the 28 kDa band in immunoblot analysis and the kallikrein ImmunoCAP measurements described in Example 3 above, revealing a close correlation.

Figure 7:
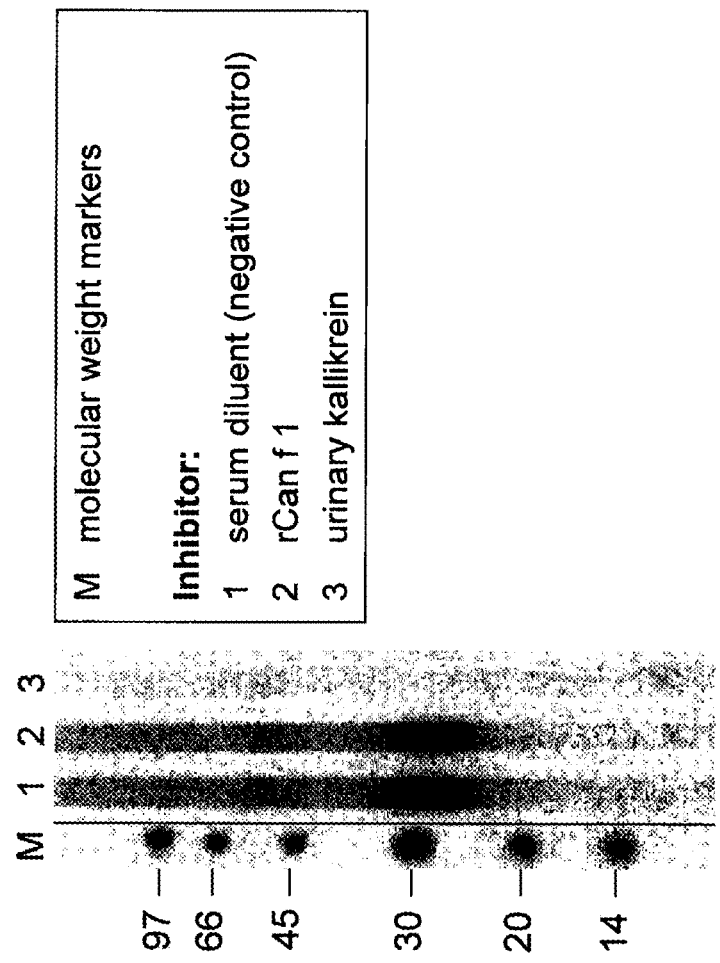
FIG. 7 shows specific immunoblot inhibition of the 28 kDa protein band by purified dog urinary kallikrein. Lane M contains molecular weight marker proteins.

In order to directly examine the relationship between urinary kallikrein and the 28 kDa band in dog dander, an immunoblot inhibition experiment was performed. A serum mono-reactive to the 28 kDa band was preincubated 2 hrs at room temperature with either purified urinary kallikrein or rCan f 1, both at a final concentration of 100 μg/mL, or with serum diluent. Membrane strips carrying immunoblotted non-reduced dog dander extract were then subjected to the preincubated serum samples and IgE binding was analysed as described above. The experiment revealed that IgE binding to the 28 kDa band in dog dander was completely abolished by serum preincubation with kallikrein whereas it remained unaffected by preincubation with both rCan f 1 and buffer alone (FIG. 7).

Taken together, the results described in this example demonstrated the presence in dog dander extract of a protein displaying close electrophoretic and immunological similarity to urinary kallikrein.

Example 6

Partial Purification and Identification of Kallikrein in Dog Dander

Figure 8:
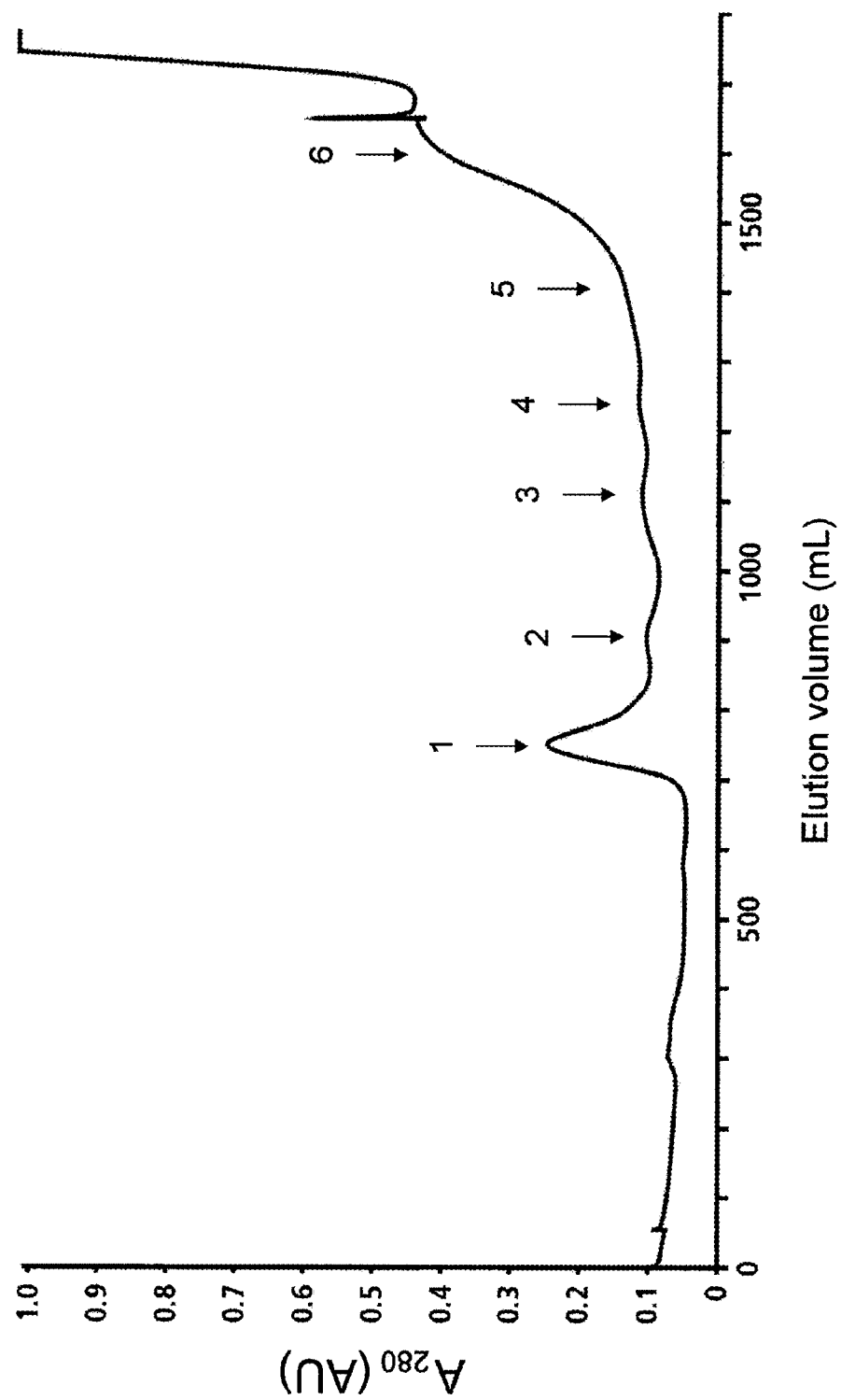
FIG. 8 shows the first step of purification of kallikrein from dog dander, by size exclusion chromatography. Six fractions (labeled 1-6) indicated in the figure were analysed for IgE binding activity.

The kallikrein-like protein from dog dander was purified by SEC and RPC for biochemical identification. Three grams of dog dander (Allergon, Välinge, Sweden) was extracted in a 100 mL of MBS by end-over-end rotation for 3 hrs at room temperature. After centrifugation at 20,000×g and concentration using an Amicon filter (PM-10, Millipore, Billerica, Mass., USA), the extract was applied to an XK50/100 Superdex 75 column (GE Healthcare Biosciences) and eluted using MBS (FIG. 8). Fractions from six peaks (indicated 1-6 in FIG. 8) were pooled and analysed for allergen activity. The protein content of each fraction was immobilized on ImmunoCAP (Phadia, Uppsala, Sweden) solid phase and its IgE antibody binding activity tested using eight sera from dog dander sensitized individuals, as indicated in Table 4. Most of these sera were selected as having high IgE binding to dog dander extract but relatively low binding to either of rCan f 1, rCan f 2 and nCan f 3. From Table 4 it is evident that peak 3 from the SEC separation contained the highest level of IgE binding activity of the six peaks tested. This pool was selected for further purification.

Figure 9:
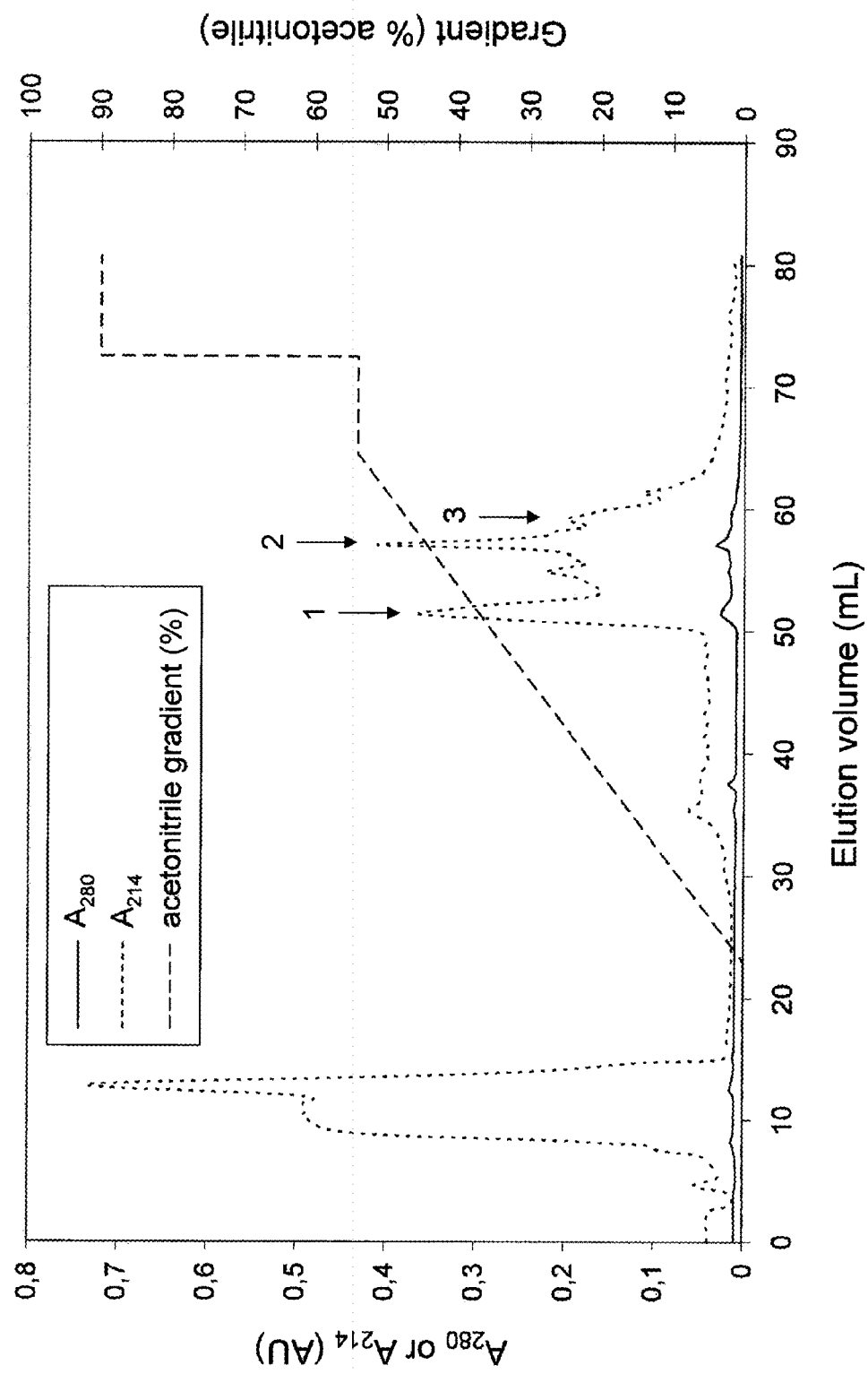
FIG. 9 shows the second step of purification of kallikrein from dog dander, by reversed phase chromatography. Top fractions of three peaks indicated in the figure (labeled 1-3) were analysed for IgE antibody binding activity.

After adding TFA to a final concentration of 0.065%, the pool was applied to a ST4.6/100 Source 15 RPC column (GE Healthcare Biosciences) and elution was performed using a linear, 0-54% gradient of acetonitril in water containing 0.05% TFA (FIG. 8). Analysis of allergen reactivity of the three peaks indicated in FIG. 9 was performed using five sera, selected by the criteria described above, The results of the analysis (Table 5) clearly showed that peak 1 contained the highest level of IgE antibody binding. Reducing SDS-PAGE analysis of this peak revealed the presence of 10 kDa, 18 kDa and 23 kDa protein bands (not shown).

The three band present in peak 1 were excised from the gel and subjected to in-gel digestion and mass spectrometric analysis as described in Example 2 above. While the 23 kDa band was identified as Can f 1, both the 10 kDa and 18 kDa bands were identified as dog prostatic kallikrein (Accession no P09582) after PSD analysis of selected peptides m/z=1004.52 and m/z=1632.98, respectively.

Further, the two 10 kDa and 18 kDa bands were eluted from excised gel bands and subjected to N-terminal amino acid sequencing. The resulting sequences, xIGGRExLKN (SEQ ID NO: 7) and AVxRPGEDRx (SEQ ID NO: 8), where "x" represents unresolved residues, matched residues 25-34 and 108-117 of the canine prostatic kallikrein precursor sequence. Accession no P09582.

The results described in this example demonstrated that a protein with a primary structure identical or closely related to prostatic kallikrein is present in dog dander.

Example 7

Similar IgE Antibody Reactivity to Kallikrein from Dog Dander and Urine

Figure 10:
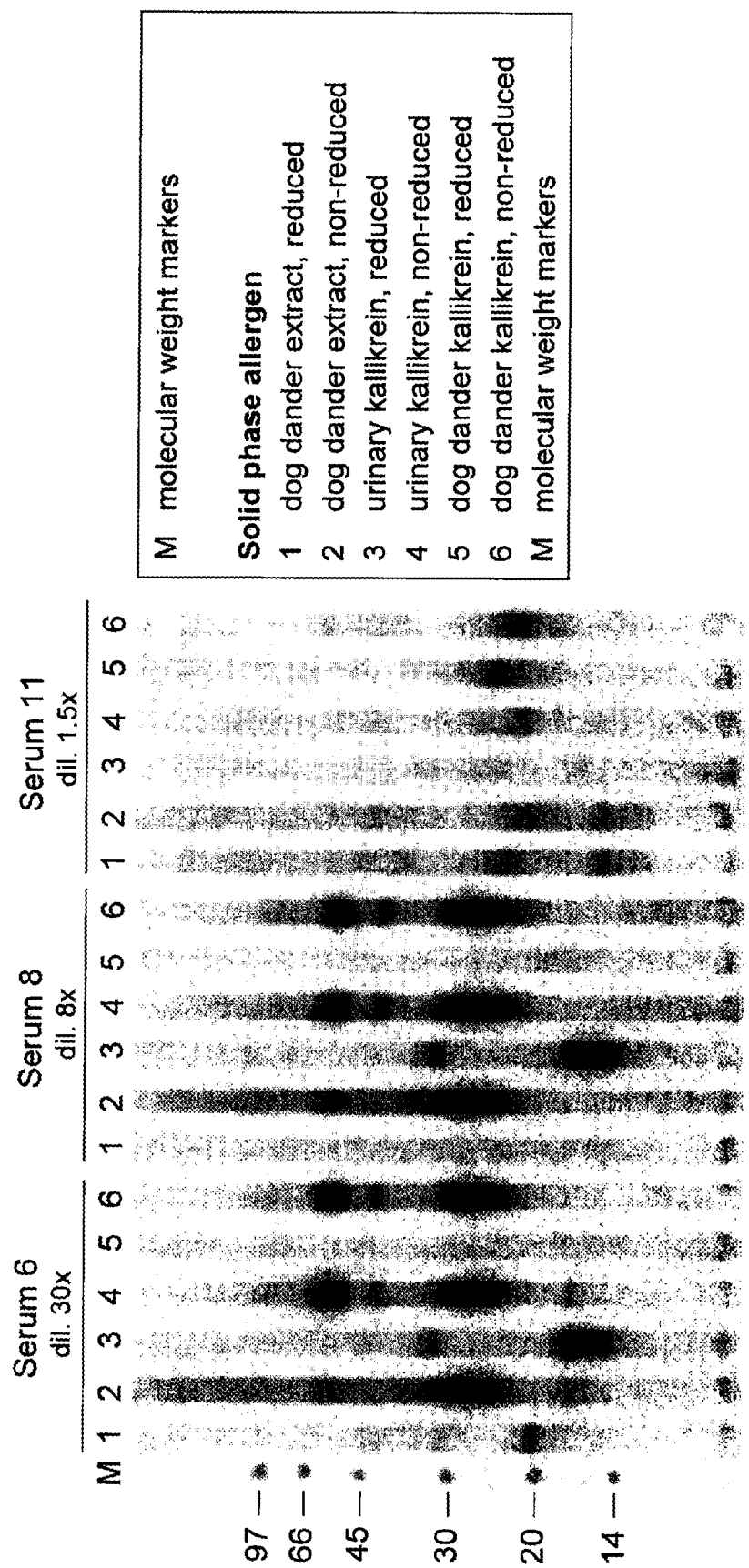
FIG. 10 shows a comparative immunoblot analysis specific IgE antibody binding to dog dander extract, purified urinary kallikrein and partially purified kallikrein from dog dander. Two kallikrein-reactive sera (no. 6 and 8) and one kallikrein non-reactive serum (no. 11) were used. Both reduced and non-reduced forms of the allergen preparations were analysed, as indicated in the legend. Lane M contains molecular weight marker proteins.

To compare the IgE antibody binding activity of kallikrein from dog urine and dander, two kallikrein-reactive sera (sera no 6 and 8 from Table 2) and one kallikrein non-reactive serum (no 11) were used in immunoblot analysis of non-reduced samples of dog dander extract, purified urinary kallikrein and partially purified kallikrein from dog dander (FIG. 10). The two kallikrein-reactive sera displayed IgE binding to a 28 kDa band in all three preparations, indicating that IgE binding at 28 kDa in dog dander extract is due to kallikrein. In addition, it was evident that the dominant reactivity to the 28 kDa band in purified urinary kallikrein coincided with the Coomassie stained protein bands of the same preparation. IgE binding to a band of about 55 kDa in the non-reduced kallikrein preparations is consistent with the notion in Example 1 above, of a putative dimer of kallikrein. The serum that was kallikrein non-reactive according to ImmunoCAP showed no IgE binding to the 28 kDa band in any of the three allergen preparations analysed.

The immunoblotting reactivity to reduced kallikrein-containing samples was considerably weaker than to non-reduced samples. Only the purified urinary kallikrein preparation, which had a higher kallikrein concentration than the other preparations analysed, gave rise to detectable IgE binding to the 18 kDa band formed upon reduction.

The observation that the immune reactivity to purified urinary kallikrein in immunoblot analysis was directed against the major protein band at 28 kDa served to support the validity of the experimental kallikrein ImmunoCAP test, in that its IgE binding was not caused a contaminant of the protein preparation used. The results further show that at least some IgE binding epitopes on kallikrein are sensitive to reduction of the molecule, as indicated by the weaker antibody binding to the 10 kDa and 18 kDa subunits, as compared to the 28 kDa unreduced molecule.

Example 8

Assessment of IgE-Binding Properties of a Modified Kallikrein or a Variant or Fragment of Kallikrein (Analyte)

The analyte is immobilized to a solid support, such as ImmunoCAP (Phadia, Uppsala, Sweden). Serum samples from at least three representative human patients sensitized to the relevant species and showing IgE reactivity to kallikrein from that species are incubated for 3 h at room temperature with kallikrein at a final concentration of 100 µg/mL and, in parallel as negative controls, with buffer alone and the non-allergenic maltose binding protein (MBP) of *E. coli*. The samples are then analysed for IgE binding to ImmunoCAP (Phadia, Uppsala, Sweden) tests carrying immobilized analyte to study whether preincubation with kallikrein specifically inhibits or significantly lowers IgE binding.

Example 9

Purification of Kallikrein from Dog Urine by Hydrophobic Interaction Chromatography (HIC)

A pooled sample of dog urine was filtered through a 5 µm and a 0.45 µm filter under nitrogen pressure. All chromatographic operations were performed with an ÄKTA Explorer 100 Air system (GE Healthcare Biosciences, Uppsala, Sweden). Four aliquots of 120 ml filtered dog urine was buffer exchanged using a Sephadex G-25 column (GE Healthcare Biosciences, Uppsala, Sweden) (column volume 461 ml), with cleaning of the column after each run. Buffer used: 50 mM Na-phosphate, 1 M $(NH_4)_2SO_4$, 0.02% $NaN_3$, pH=7. The sample (about 505 ml) was then filtered through a 0.45 µm filter and applied to the HIC column (HiPrep Phenyl FF (high sub), 20 ml, GE Healthcare Biosciences, Uppsala, Sweden). Buffers used for HIC separation were: A) 50 mM Na-phosphate, 1 M $(NH_4)_2SO_4$, 0.02% $NaN_3$, pH=7, and B) 50 mM Na-phosphate, 0.02% $NaN_3$, pH=7. The flow through fraction (containing kallikrein) was collected in 10 ml fractions (Frac 950) at a flow rate of 5 ml/min and the flow through fractions were then pooled. The adsorbed material was eluted in a step gradient using 100% buffer B.

The fractions were analyzed using a BCA (bicinchoninic acid) assay, as well as SDS-PAGE (non reduced samples, silver staining). SDS-PAGE under non-reducing conditions revealed that kallikrein was found in the flow-through fractions which thus were pooled for further processing.

Two aliquots of about 125 ml and one aliquot of about 87 ml of the pooled HIC flow through fractions were buffer exchanged with a Sephadex G-25 SF column (GE Healthcare Biosciences, Uppsala, Sweden) to a buffer with the composition 20 mM Na-phosphate, 0.02% $NaN_3$, pH=8. The kallikrein-pool (456 ml) was then concentrated on an Amicon cell (350 ml, Millipore filter, PBCC, cutoff 5000 kDa, diameter 76 mm) to a volume of about 43 ml. Using BCA assay, the protein concentration in the final pool was determined to be 0.9 mg/ml (in 43 ml=totally 38.7 mg) The sample applied to the HIC-column contained 101 mg protein which yielded a recovery of 38% of kallikrein after the HIC purification.

The purity of the kallikrein preparation was assessed by analytical gel filtration on a Superdex 75 HR 10/30 column in an ÄKTA purifier XT10 system. For this experiment the sample volume was 100 µl and the buffer was 10 mM Na-phosphate, 150 mM NaCl, 0.02% $NaN_3$, pH=7.4.

Example 10

Identification and Characterization of Kallikrein from Dog Urine by the Use of Electrophoresis and Mass Spectrometry Using electrophoresis the following samples were compared on the same gel, applying colloidal coomassie brilliant blue (CBB) staining:
1. A standard molecular weight marker
2. Dog urine
3. HIC-eluted material (reduced)
4. HIC flow-through fraction (reduced)
5. HIC flow-through fraction (non-reduced)
6. HIC-eluted material (non-reduced)

For samples 2, 3 and 6, a large number of proteins were detected. However, in sample 4 (reduced HIC flow-through fraction), only two main bands could be seen. These two bands were later, by the use of MALDI-TOF(-TOF) analysis (see below), found to correspond to two different variants of the kallikrein protein (as a result of proteolysis at R107, due to arginin-esterase activity). In sample 5 (non-reduced HIC flow-through fraction), seven distinct bands were detected and all bands were found to correspond to different variants of the kallikrein protein by the use of MALDI-TOF(-TOF) analysis (see below). Kallikrein comprises 12 cystein-residues, therefore the formation of different variants is possible under non-reducing conditions due to formation of cystein-cystein bridges. Thus, the formation of for example dimers, trimers etc is likely to happen under non-reducing conditions.

SDS-PAGE Conditions, Trypsin Digestion and MALDI-TOF-TOF Analysis:

Diluted samples were prepared using a SDS-PAGE cleanup kit according to the procedure recommended in the manual from the supplier (GE Healthcare, Uppsala, Sweden). The gels were run in a MES buffer at 200 V for 35 minutes. Reduced and non-reduced samples were run in separate aggregates. Staining was done overnight with colloidal CBB (de-staining was later done using water immersion for about 5 hours). Samples were manually picked from the gel using a pipette tip, and treated according to a standard protocol (using ethanol instead of acetonitrile), incubated with 12.5 ng/μl trypsin over night at 37° degrees Celsius, 0.5 μl of the digested samples was applied on the target plate for the MALDI system and mixed with 0.5 μl MALDI matrix solution (saturated solution of HCCA in 50% acetonitril, 0.1% TFA). All samples were analyzed, using a MALDI-TOF-TOF (Bruker Daltonics, Bremen, Germany) mass spectrometer. To identify proteins matching PMF results obtained, the MSDB database was searched using a Mascot server (Matrixscience, London, UK). MS-MS analysis was performed on selected peptides. External calibration was performed using a peptide calibration standard (Bruker Daltonics). Database searches were run using the following search criteria:

Taxonomy: mammalia

Mass tolerance: 100 ppm

Allowing for oxidized methionines and 1 missed cleavage.

Kallikrein Sequence from the Database:

MWFLALCLAMSLGWTGAEPHFQPRIIGGRECLKN-SQPWQVAVYHNGEFACGGVLV NPEWVLTAAII-CANSNCEVWLGRIINLSESEDEGQLVQVRKSFIH-PLYKTKVPR
AVIRPGEDRSHDLMLLHLEEPAKITKAVRVMDLPK-KEPPLGSTCYVSGWGSTDPETI FHPGSLQCVDLKLL-SNNQCAKVYTQKVTKFMLCAGVLEGKKDTCK-GDSGGPLICD
GELVGITSWGATPCGKPQMPSLYTRVMPHLM-WIKDTMKANT (SEQ ID NO: 1) (Peptide sequences identified by MALDI-TOF (/TOF) MS (/MS) in bold italic.)

Example 11

Cloning, Purification and Assessment of the IgE Binding Activity of Recombinant Dog Kallikrein Expressed in *Pichia pastoris*

In order to verify the identification and importance of urinary kallikrein as a dog allergen, the protein was produced as a recombinant allergen using *Pichia pastoris* as expression host, purified and analysed for IgE antibody binding activity.

Preparation of Synthetic Gene Construct Encoding Dog Urinary Kallikrein

A synthetic dog urinary kallikrein gene was designed by back-translating into nucleotide sequence the part of the reported amino acid sequence of dog prostatic arginine esterase (urinary kallikrein, Acc. No. P09582) corresponding to the mature protein. The nucleotide sequence was designed for optimal codon usage and synonymously adjusted to minimize secondary structures and eliminate or add restriction enzyme sites as desired. Oligonucleotides corresponding to the final coding sequence were obtained and assembled, and the full-length synthetic gene amplified by PCR and cloned into the XhoI and SalI sites of vector pPICZ A (Invitrogen, Carlsbad, Calif., USA), adding a C-terminal hexahistidine tag to enable protein purification by immobilised metal ion affinity chromatography (IMAC). The plasmid DNA construct was linearized by Sac I digestion and transformed into *P. pastoris* strain X-33 for homologous recombination into the chromosomal AOX1 locus.

Expression and Purification of Recombinant Dog Kallikrein-2

The recombinant protein was produced in *Pichia pastoris* strain X-33 (Invitrogen) using a 7 L bioreactor (Belach Bioteknik, Solna, Sweden). A rich broth medium (20 g/L peptone, 10 g/L yeast extract, 3.4 g/L yeast nitrogen base, 10 g/L ammonium sulfate, 0.4 mg/L biotin and 0.1 M potassium phosphate) was used and the cultivation carried out at 30° C. Expression was induced and maintained by feeding methanol to the culture to a steady-state concentration of 0.1% (v/v). After 70 hrs of fermentation, the culture was harvested by centrifugation at 10 000 g for 10 min at +4° C. and the supernatant recovered for protein purification.

The supernatant was conditioned for purification by adding imidazole to 5 mM and NaCl to 0.15 M and adjusting the pH to 7.2 using Tris base(s) before applying it to a Streamline 25 chelating column (GE Healthcare Biosciences), charged with $NiSO_4$ according to the manufacturer's recommendation. After loading, the column was washed in separate steps with 20 mM and 60 mM imidazole and the recombinant protein was then eluted with 500 mM imidazole, all in a buffer composed of 20 mM Tris-HCl pH 8.0 and 0.15 M NaCl.

Further purification of the recombinant protein was performed using cation exchange chromatography. IMAC fractions containing recombinant kallikrein were identified by SDS-PAGE, pooled and diluted with 2 volumes of 20 mM MES pH 6.0. After adjusting pH to 6.0, the diluted pool was applied to an XK26/100 SP Sepharose FF column (GE Healthcare Biosciences). The column was then washed with 2 column volumes of 0.15 M NaCl in 20 mM MES pH 6.0 and the recombinant protein eluted with 0.30 M NaCl in the same buffer. The protein concentration was determined from absorbance at 280 nm, using a calculated extinction coefficient of 1.46 per mg/mL.

Figure 11:
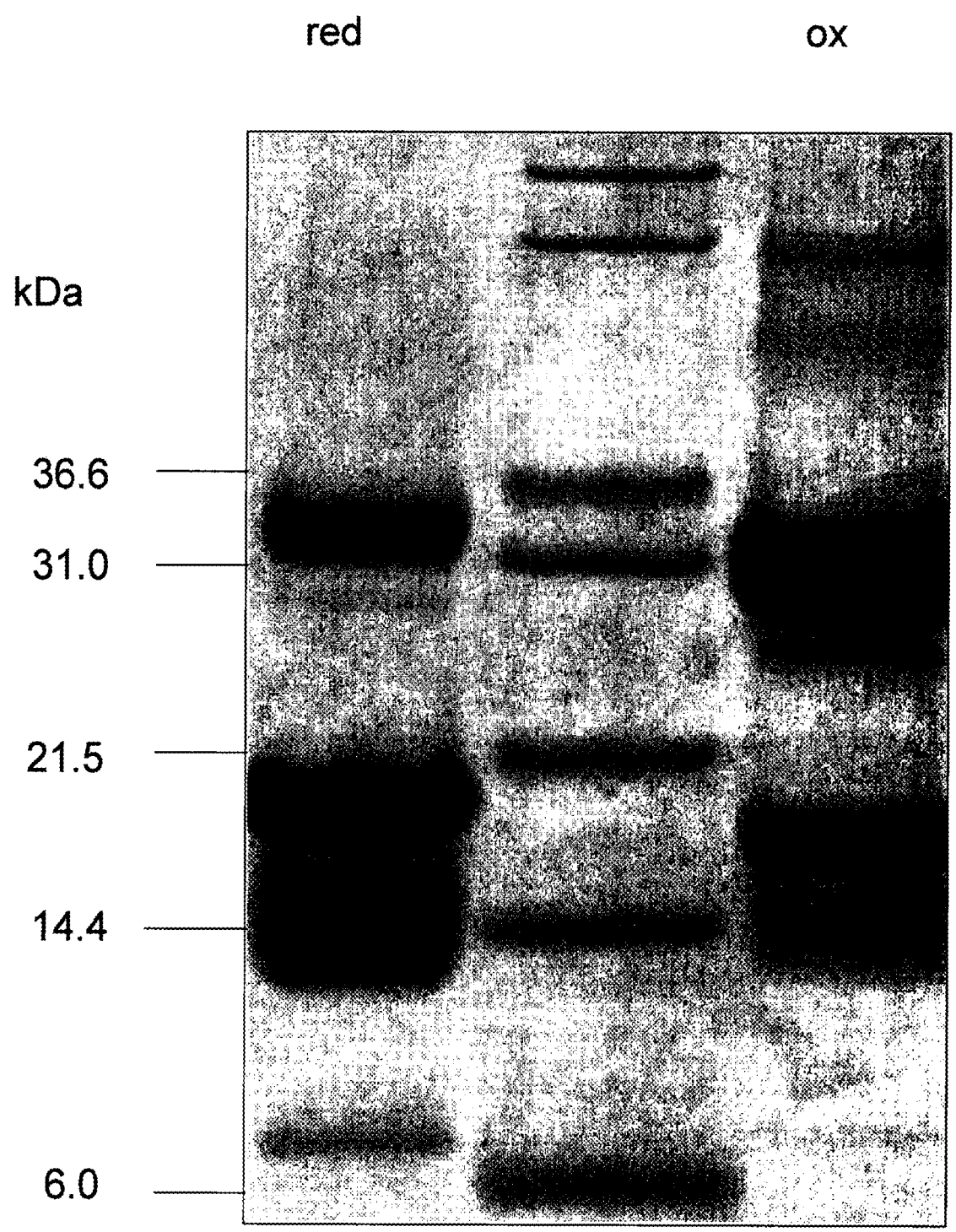
FIG. 11 shows SDS Page analysis of purified recombinant dog urinary kallikrein.

Although the synthetic kallikrein gene construct was designed to direct the production of a single polypeptide chain, the protein purified from the culture medium was found to have undergone a partial cleavage into 18 kDa and 12 kDa chains (FIG. 11), similar to the processing of natural urinary kallikrein. Indeed, N-terminal sequencing revealed that the recombinant kallikrein had been cleaved at the same position as the natural molecule (data not shown).

Figure 12:
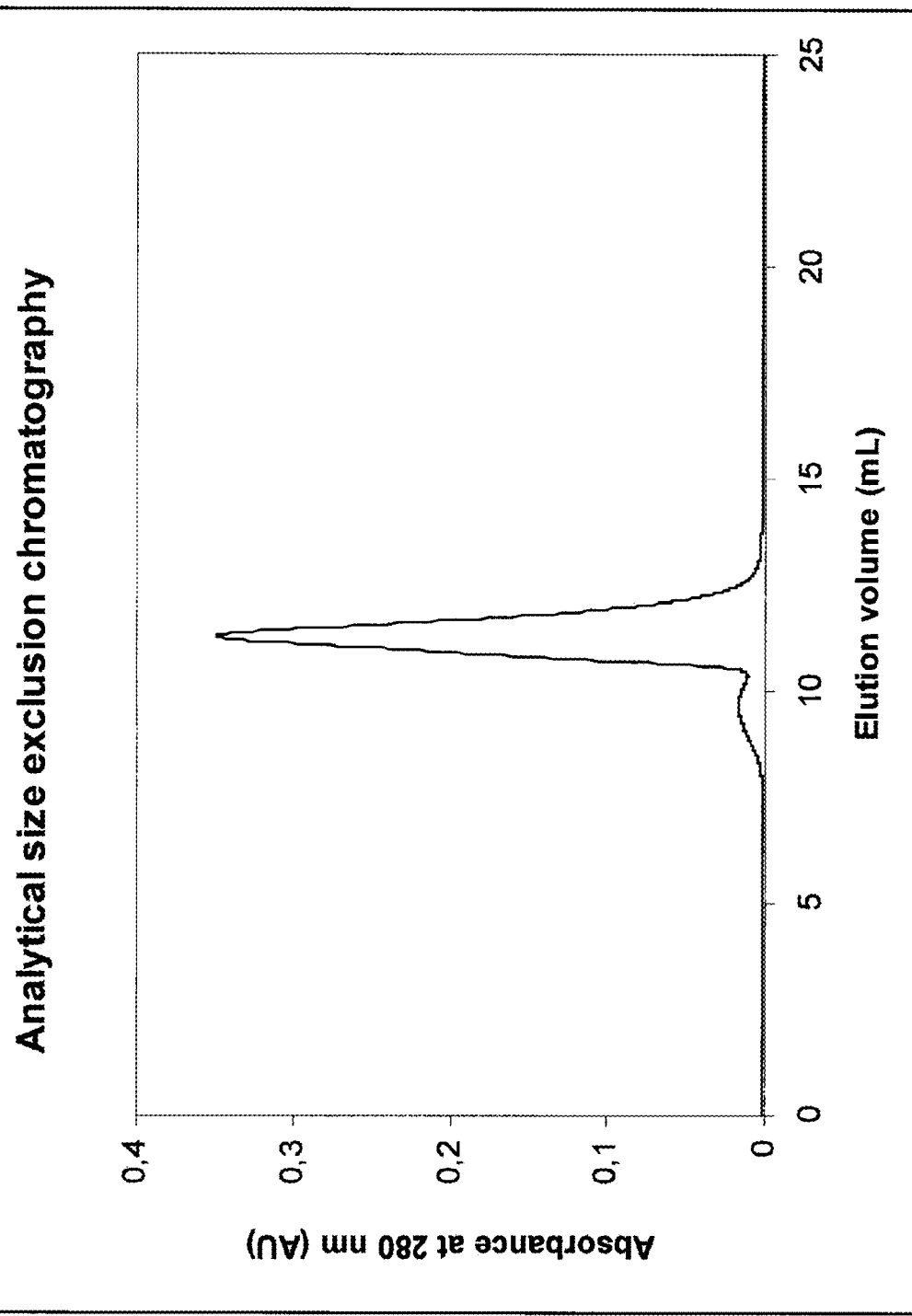
FIG. 12 shows analytical gelfiltration analysis of purified recombinant dog urinary kallikrein.

To assess the aggregation state and integrity of the recombinant protein under physiological conditions, a sample of the preparation was subjected to analytical size exclusion chromatography. As shown in FIG. 12, the chromatogram was dominated by a single symmetrical peak, corresponding to a molecular weight of 34 kDa as defined by the LMW Calibration Kit (GE Healthcare Biosciences). The analysis demonstrated that the recombinant protein, despite its partial processing, was held together in solution and existed in a homogeneous, most likely monomeric, aggregation state.

IgE Binding Activity of Recombinant Kallikrein

The immunological activity of the recombinant kallikrein produced was assessed in comparison to the natural protein purified from dog urine. The two proteins were immobilised separately on ImmunoCAP® solid phase and their in vitro IgE binding capacity was examined using the 37 serum samples from dog allergic subjects described in Example 3 above.

Figure 13:
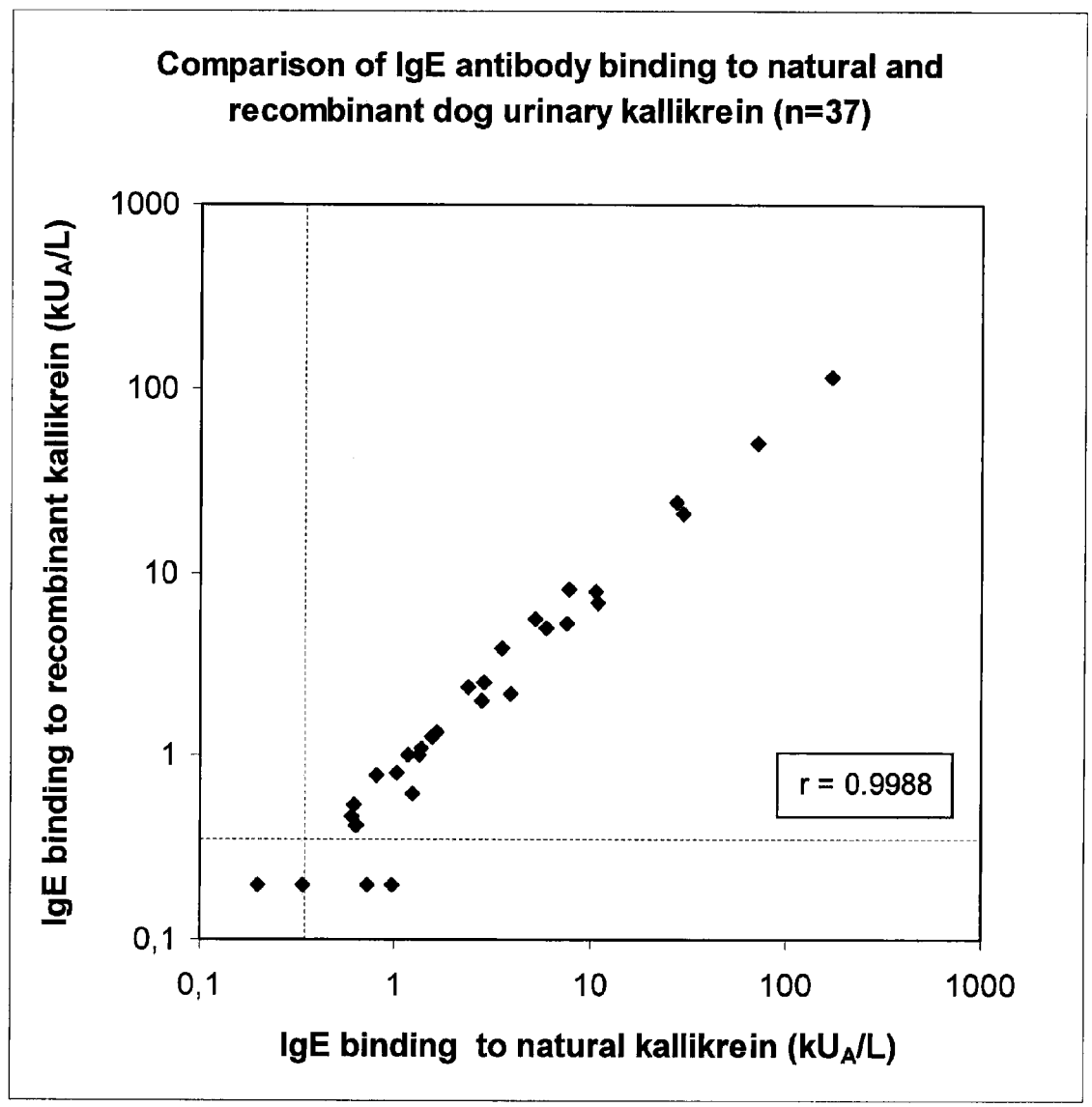
FIG. 13 shows a comparison of specific IgE antibody binding activity of natural and recombinant dog urinary kallikrein.

As can be seen in FIG. 13, the two datasets showed a very strong correlation (r=0.9988), demonstrating that the recombinant kallikrein produced closely resembled natural urinary kallikrein with respect to IgE antibody binding. Drawing from the complete absence of any other dog-derived protein in the recombinant protein preparation, it can be further noted that the results eliminate any possible doubt as to the identity of the active component of the natural kallikrein preparations described in the previous examples.

REFERENCES

1. Custovic A, Green R, Taggart S C O, Smith A, Pickering C A C, Chapman M D et al. Domestic allergens in public places II: dog (Can f 1) and cockroach (Bla g 2) allergens in dust and mite, cat, dog and cockroach allergens in the air in public buildings. Clinical & Experimental Allergy 1996; 26:1246-1252.
2. Spitzauer S, Schweiger C, Anrather J, Ebner C, Scheiner O, Kraft D et al. Characterisation of dog allergens by means of immunoblotting. International Archives of Allergy and Immunology 1993; 100:60-67.
3. Spitzauer S. Allergy to mammalian proteins: At the borderline between foreign and self? [Review]. International Archives of Allergy and Immunology 1999; 120: 259-269.
4. de Groot H, Goei K G H, van Swieten P, Aalberse R C. Affinity purification of a major and a minor allergen from dog extract: serologic activity of affinity-purified Can f I and of Can f I-depleted extract. Journal of Allergy and Clinical Immunology 1991; 87:1056-1065.
5. Konieczny A, Morgenstern J P, Bizinkauskas C B, Lilley C H, Brauer A W, Bond J F et al. The major dog allergens, Can f 1 and Can f 2, are salivary lipocalin proteins: cloning and immunological characterization of the recombinant forms. Immunology 1997; 92:577-586.
6. Boutin Y, Hebert H, Vrancken E R, Mourad W. Allergenicity and cross-reactivity of cat and dog allergenic extracts. Clinical Allergy 1988; 18:287-293.
7. Saarelainen S, Taivainen A, Rytkonen-Nissinen M, Auriola S, Immonen A, Mantyjarvi R et al. Assessment of recombinant dog allergens Can f 1 and Can f 2 for the diagnosis of dog allergy. Clinical & Experimental Allergy 2004; 34:1576-1582.
8. Cabanas R, Lopez-Serrano M C, Carreira J, Ventas P, Polo F, Caballero M T et al. Importance of albumin in cross-reactivity among cat, dog and horse allergens. Journal of Investigational Allergology & Clinical Immunology 2000; 10:71-77.
9. Bayard C, Holmquist L, Vesterberg O. Purification and identification of allergenic alpha (2 u)-globulin species of rat urine. Biochim Biophys Acta 1996; 1290:129-134.
10. Ohman J L. Allergy in man caused by exposure to mammals. J Am Vet Med Assoc 1978; 172:1403-1406.
11. Schumacher M J. Characterization of allergens from urine and pelts of laboratory mice. Mol Immunol 1980; 17:1087-1095.
12. Siraganian R P, Sandberg A L. Characterization of mouse allergens. Journal of Allergy and Clinical Immunology 1979; 63:435-442.
13. Taylor A N, Longbottom J L, Pepys J. Respiratory allergy to urine proteins of rats and mice. Lancet 1977; 2:847-849.
14. Hoffman D R. Dog and cat allergens: urinary proteins or dander proteins? Annals of Allergy 1980; 45:205-206.
15. Hiller R, Laffer S, Harwanegg C, Huber M, Schmidt W M, Twardosz A et al. Microarrayed allergen molecules: diagnostic gatekeepers for allergy treatment. FASEB Journal 2002; 16:414-416.
16. Valenta R, Lidholm J, Niederberger V, Hayek B, Kraft D, Gronlund H. The recombinant allergen-based concept of component-resolved diagnostics and immunotherapy (CRD and CRIT). Clinical & Experimental Allergy 1999; 29:896-904.
17. Cromwell O, Fiebig H, Suck R, Kahlert H, Nandy A, Kettner J et al. Strategies for recombinant allergen vaccines and fruitful results from first clinical studies. Immunol Allergy Clin North Am 2006; 26:261-281, vii.
18. Gafvelin G, Thunberg S, Kronqvist M, Gronlund H, Gronneberg R, Troye-Blomberg M et al. Cytokine and antibody responses in birch-pollen-allergic patients treated with genetically modified derivatives of the major birch pollen allergen Bet v 1. International Archives of Allergy and Immunology 2005; 138:59-66.
19. Jutel M, Jaeger L, Suck R, Meyer H, Fiebig H, Cromwell O. Allergen-specific immunotherapy with recombinant grass pollen allergens. Journal of Allergy and Clinical Immunology 2005; 116:608-613.
20. Mahler V, Vrtala S, Kuss O, Diepgen T L, Suck R, Cromwell O et al. Vaccines for birch pollen allergy based on genetically engineered hypoallergenic derivatives of the major birch pollen allergen, Bet v 1. Clinical & Experimental Allergy 2004; 34:115-122.
21. Weidinger S, Mayerhofer A, Raemsch R, Ring J, Kohn F M. Prostate-specific antigen as allergen in human seminal plasma allergy. Journal of Allergy and Clinical Immunology 2006; 117:213-215.
22. Demoly P, Lebel B, Arnoux B. Allergen-induced mediator release tests. Allergy 2003; 58:553-558.
23. Ebo D G, Hagendorens M M, Bridts C H, Schuerwegh A J, De Clerck L S, Stevens W J. In vitro allergy diagnosis: should we follow the flow? [Review]. Clinical & Experimental Allergy 2004; 34:332-339.
24. Shevchenko A, Wilm M, Vorm O, Mann M. Mass spectrometric sequencing of proteins silver-stained polyacrylamide gels. Anal Biochem 1996; 68:850-858.
25. Frenette G, Deperthes D, Tremblay R R, Lazure C, Dube J Y. Purification of enzymatically active kallikrein hK2 from human seminal plasma. Biochim Biophys Acta 1997; 1334:109-115.
26. Marknell DeWitt A, Niederberger V, Lehtonen P, Spitzauer S, Sperr W R, Valent P et al. Molecular and immunological characterization of a novel timothy grass (*Phleum pratense*) pollen allergen, Phl p 11. Clinical & Experimental Allergy 2002; 32:1329-1340.
27. van Eijk H M, Rooyakkers D R, van Acker B A, Soeters P B, Deutz N E. Automated isolation of high-purity plasma albumin for isotope ratio measurements. J Chromatogr B Biomed Sci App 1999; 731:199-205.

TABLE 1

Specific IgE binding activity of three size exclusion chromatography peaks of dog urine

| Serum | Peak no | | |
|---|---|---|---|
| | 1 | 2 | 3 |
| A | 0.72 | 75.87 | neg |
| B | 0.62 | 0.59 | neg |

TABLE 1-continued

Specific IgE binding activity of three size exclusion chromatography peaks of dog urine

| Serum | Peak no 1 | Peak no 2 | Peak no 3 |
|---|---|---|---|
| C | 1.32 | 14.71 | 0.35 |
| D | 1.32 | 14.47 | neg |
| E | 1.08 | 7.98 | neg |
| F | 0.81 | 6.38 | neg |
| G | 0.48 | 2.35 | neg |
| H | 0.54 | 1.83 | neg |

The protein content of pooled fractions of each peak was immobilized on immunoCAP solid phase for analysis of IgE binding activity, using serum samples from 8 dog allergic subjects.
Values given are $kU_A/L$ of specific IgE.

TABLE 2

Specific IgE analysis of sera from 37 dog allergic subjects

| Serum | dog dander | rCan f 1 | rCan f 2 | nCan f 3 | kallikrein |
|---|---|---|---|---|---|
| 1 | 44.5 | 32.14 | neg | neg | 0.73 |
| 2 | 27.1 | 9.60 | 4.36 | neg | 7.48 |
| 3 | 2.66 | 1.21 | 0.60 | 0.67 | neg |
| 4 | 1.89 | neg | neg | neg | 0.74 |
| 5 | 3.86 | 1.38 | neg | neg | 1.60 |
| 6 | >100 | neg | neg | neg | >100 |
| 7 | 5.92 | neg | neg | neg | 5.88 |
| 8 | 16 | neg | neg | neg | 24.98 |
| 9 | 5.2 | neg | neg | neg | neg |
| 10 | 3.14 | 1.92 | neg | neg | 0.89 |
| 11 | 2.9 | 0.84 | neg | neg | neg |
| 12 | 4.5 | 1.30 | neg | neg | 1.53 |
| 13 | 1.9 | neg | neg | neg | 1.61 |
| 14 | 4.31 | neg | neg | neg | 2.83 |
| 15 | 2.75 | neg | neg | neg | 2.68 |
| 16 | 1.64 | neg | neg | neg | 1.50 |
| 17 | >100 | 11.04 | 2.21 | 28.20 | 0.72 |
| 18 | 2.2 | neg | neg | neg | 1.48 |
| 19 | 4.38 | 1.78 | 1.19 | neg | 0.49 |
| 20 | 3.19 | neg | neg | neg | 1.88 |
| 21 | 9.86 | neg | neg | neg | 11.17 |
| 22 | 3.43 | 1.19 | neg | neg | neg |
| 23 | 1.58 | 3.75 | neg | neg | neg |
| 24 | 2.27 | neg | neg | neg | neg |
| 25 | 1.57 | neg | 0.80 | neg | neg |
| 26 | 10.8 | neg | neg | 19.09 | 7.46 |
| 27 | 4.6 | neg | neg | neg | 3.95 |
| 28 | 34.8 | neg | neg | 1.45 | 25.32 |
| 29 | 2.39 | 1.06 | neg | neg | 1.56 |
| 30 | 8.85 | neg | neg | neg | 8.26 |
| 31 | 21.5 | 5.83 | neg | 8.76 | 1.34 |
| 32 | 3.17 | neg | neg | neg | 2.71 |
| 33 | 57.5 | 12.25 | neg | neg | 81.53 |
| 34 | 8.07 | 2.32 | neg | neg | neg |
| 35 | 22.1 | 4.04 | 6.06 | 1.97 | 7.28 |
| 36 | 3.85 | 0.44 | 1.22 | neg | 0.66 |
| 37 | 7.41 | 1.78 | 1.36 | neg | 5.00 |

Specific IgE was determined using immunoCAP tests carrying immobilized dog dander extract, rCan f 1, rCan f 2, nCan f 3 and dog urinary kallikrein. Values given are $kU_A/L$ of specific IgE.
Values below a cut-off of 0.35 $kU_A/L$ are assigned as negative.

TABLE 3

Prevalence of specific IgE reactivity among 37 dog allergic subjects

| | dog dander | rCan f 1 | rCan f 2 | nCan f 3 | kallikrein |
|---|---|---|---|---|---|
| in total | 37 | 37 | 37 | 37 | 37 |
| negative | 0 | 19 | 29 | 31 | 8 |
| >0.35 $kU_A/L$ of specific IgE | 37 | 18 | 8 | 6 | 29 |
| >3.5 $kU_A/L$ of specific IgE | 22 | 7 | 2 | 3 | 12 |

The data comprise a summary of the results shown in Table 2

TABLE 4

Specific IgE binding activity of six size exclusion chromatography peaks of dog dander extract

| Serum | Peak no. 1 | 2 | 3 | 4 | 5 | 6 |
|---|---|---|---|---|---|---|
| a | 1.10 | 1.50 | 4.11 | 0.70 | 0.63 | 0.61 |
| b | 1.34 | 1.66 | 5.61 | 0.70 | neg | neg |
| c | 1.40 | 1.70 | 2.51 | 1.71 | 1.43 | 1.31 |
| d | 0.89 | 1.06 | 2.29 | 0.47 | 0.37 | 0.36 |

The protein content of top fractions of each peak was immobilized on immunoCAP solid phase for analysis of IgE binding activity, using serum samples from 4 dog allergic subjects. Values given are $kU_A/L$ of specific IgE.

TABLE 5

Specific IgE binding activity of three reversed phase chromatography peaks of dog dander extract

| Serum | Peak no. 1 | 2 | 3 |
|---|---|---|---|
| a | 15.82 | neg | neg |
| b | 14.00 | 0.75 | 0.42 |
| d | 4.77 | 0.60 | 0.42 |
| e | 1.45 | 0.80 | 0.53 |
| f | neg | 0.94 | 1.04 |

The protein content of top fractions of each peak was immobilized on immunoCAP solid phase for analysis of IgE binding activity, using serum samples from 5 dog allergic subjects.
Values given are $kU_A/L$ of specific IgE.

The invention claimed is:

1. A method for treatment of a Type I allergy in a mammal, comprising administering to an individual in need of such treatment a polypeptide of SEQ ID NO: 1 or the mature protein, amino acids 25-260, of the polypeptide of SEQ ID NO: 1, or a fragment of the polypeptide or the mature protein, which fragment shares epitopes for antibodies with the polypeptide or the mature protein, respectively.

2. The method of claim 1, wherein the mature protein, amino acids 25-260, of the polypeptide of SEQ ID NO: 1, is administered.

3. The method of claim 1, wherein said mammal is a primate.

4. The method of claim 1, wherein said mammal is selected from the group consisting of humans, cats, horses, cows, pigs, rats and mice.

5. The method according to claim 1, wherein the polypeptide is purified from dog urine.

6. The method according to claim 1, wherein the polypeptide is recombinantly produced.

7. The method according to claim 1, wherein the fragment is administered and the fragment has at least 50 amino acid residues.

8. The method according to claim 1, wherein the fragment is administered and the fragment has at least 75 amino acid residues.

9. The method according to claim 1, wherein the fragment is administered and the fragment has at least 100 amino acid residues.

10. The method according to claim 1, wherein the fragment is administered and the fragment has a sequence identity to the mature protein, amino acids 25-260, of the polypeptide of SEQ ID NO: 1 of at least 50%.

11. The method according to claim 1, wherein the fragment is administered and the fragment has a sequence identity to the mature protein, amino acids 25-260, of the polypeptide of SEQ ID NO: 1 of at least 60%.

12. The method according to claim 1, wherein the fragment is administered and the fragment has a sequence identity to the mature protein, amino acids 25-260, of the polypeptide of SEQ ID NO: 1 of at least 70%.

13. The method according to claim 1, wherein the fragment is administered and the fragment has a sequence identity to the mature protein, amino acids 25-260, of the polypeptide of SEQ ID NO: 1 of at least 80%.

14. The method according to claim 1, wherein the fragment is administered and the fragment has a sequence identity to the mature protein, amino acids 25-260, of the polypeptide of SEQ ID NO: 1 of at least 90%.

15. The method according to claim 1, wherein the fragment is administered and the fragment has a sequence identity to the mature protein, amino acids 25-260, of the polypeptide of SEQ ID NO: 1 of at least 95%.

16. The method according to claim 1, wherein the fragment is administered and the fragment is a subunit of the polypeptide of SEQ ID NO: 1 or the mature protein, amino acids 25-260, of the polypeptide of SEQ ID NO: 1 and has a molecular weight of 10±2 as measured by sodium dodecyl sulfate polyacrylamide gel electrophoresis (SDS-PAGE).

17. The method according to claim 1, wherein the fragment is administered and the fragment is a subunit of the polypeptide of SEQ ID NO: 1 or the mature protein, amino acids 25-260, of the polypeptide of SEQ ID NO: 1 and has a molecular weight of 18±2 as measured by sodium dodecyl sulfate polyacrylamide gel electrophoresis (SDS-PAGE).

18. A diagnostic kit, comprising the polypeptide of SEQ ID NO: 1 or the mature protein, amino acids 25-260, of the polypeptide of SEQ ID NO: 1, immobilized on a solid support.

* * * * *

SEQUENCE LISTING

<160> NUMBER OF SEQ ID NOS: 8

<210> SEQ ID NO 1
<211> LENGTH: 260
<212> TYPE: PRT
<213> ORGANISM: Canis familiaris

<400> SEQUENCE: 1

```
Met Trp Phe Leu Ala Leu Cys Leu Ala Met Ser Leu Gly Trp Thr Gly
1               5                   10                  15

Ala Glu Pro His Phe Gln Pro Arg Ile Ile Gly Arg Glu Cys Leu
                20                  25                  30

Lys Asn Ser Gln Pro Trp Gln Val Ala Val Tyr His Asn Gly Glu Phe
            35                  40                  45

Ala Cys Gly Gly Val Leu Val Asn Pro Glu Trp Val Leu Thr Ala Ala
        50                  55                  60

His Cys Ala Asn Ser Asn Cys Glu Val Trp Leu Gly Arg His Asn Leu
65                  70                  75                  80

Ser Glu Ser Glu Asp Glu Gly Gln Leu Val Gln Val Arg Lys Ser Phe
                85                  90                  95

Ile His Pro Leu Tyr Lys Thr Lys Val Pro Arg Ala Val Ile Arg Pro
            100                 105                 110

Gly Glu Asp Arg Ser His Asp Leu Met Leu Leu His Leu Glu Glu Pro
        115                 120                 125

Ala Lys Ile Thr Lys Ala Val Arg Val Met Asp Leu Pro Lys Lys Glu
    130                 135                 140

Pro Pro Leu Gly Ser Thr Cys Tyr Val Ser Gly Trp Gly Ser Thr Asp
145                 150                 155                 160

Pro Glu Thr Ile Phe His Pro Gly Ser Leu Gln Cys Val Asp Leu Lys
                165                 170                 175

Leu Leu Ser Asn Asn Gln Cys Ala Lys Val Tyr Thr Gln Lys Val Thr
            180                 185                 190

Lys Phe Met Leu Cys Ala Gly Val Leu Glu Gly Lys Lys Asp Thr Cys
        195                 200                 205

Lys Gly Asp Ser Gly Gly Pro Leu Ile Cys Asp Gly Glu Leu Val Gly
    210                 215                 220

Ile Thr Ser Trp Gly Ala Thr Pro Cys Gly Lys Pro Gln Met Pro Ser
225                 230                 235                 240

Leu Tyr Thr Arg Val Met Pro His Leu Met Trp Ile Lys Asp Thr Met
                245                 250                 255

Lys Ala Asn Thr
            260

<210> SEQ ID NO 2
<211> LENGTH: 11
<212> TYPE: PRT
<213> ORGANISM: Canis familiaris
<220> FEATURE:
<221> NAME/KEY: NON_TER
<222> LOCATION: (1)..(1)
<220> FEATURE:
<221> NAME/KEY: NON_TER
<222> LOCATION: (11)..(11)

<400> SEQUENCE: 2

Phe Met Leu Cys Ala Gly Val Leu Glu Gly Lys
1               5                   10

<210> SEQ ID NO 3
<211> LENGTH: 14
<212> TYPE: PRT
<213> ORGANISM: Canis familiaris
<220> FEATURE:
<221> NAME/KEY: NON_TER
<222> LOCATION: (1)..(1)
<220> FEATURE:
<221> NAME/KEY: NON_TER
```

```
<222> LOCATION: (14)..(14)

<400> SEQUENCE: 3

Ser His Asp Leu Met Leu Leu His Leu Glu Glu Pro Ala Lys
1               5                   10

<210> SEQ ID NO 4
<211> LENGTH: 8
<212> TYPE: PRT
<213> ORGANISM: Canis familiaris
<220> FEATURE:
<221> NAME/KEY: NON_TER
<222> LOCATION: (1)..(1)
<220> FEATURE:
<221> NAME/KEY: NON_TER
<222> LOCATION: (8)..(8)

<400> SEQUENCE: 4

Ser Phe Ile His Pro Leu Tyr Lys
1               5

<210> SEQ ID NO 5
<211> LENGTH: 10
<212> TYPE: PRT
<213> ORGANISM: Canis familiaris
<220> FEATURE:
<221> NAME/KEY: NON_TER
<222> LOCATION: (1)..(1)
<220> FEATURE:
<221> NAME/KEY: UNSURE
<222> LOCATION: (7)..(7)
<223> OTHER INFORMATION: Unresolved residue
<220> FEATURE:
<221> NAME/KEY: NON_TER
<222> LOCATION: (10)..(10)

<400> SEQUENCE: 5

Ile Ile Gly Gly Arg Glu Xaa Leu Lys Asn
1               5                   10

<210> SEQ ID NO 6
<211> LENGTH: 10
<212> TYPE: PRT
<213> ORGANISM: Canis familiaris
<220> FEATURE:
<221> NAME/KEY: NON_TER
<222> LOCATION: (1)..(1)
<220> FEATURE:
<221> NAME/KEY: NON_TER
<222> LOCATION: (10)..(10)

<400> SEQUENCE: 6

Ala Val Ile Arg Pro Gly Glu Asp Arg Ser
1               5                   10

<210> SEQ ID NO 7
<211> LENGTH: 10
<212> TYPE: PRT
<213> ORGANISM: Canis familiaris
<220> FEATURE:
<221> NAME/KEY: NON_TER
<222> LOCATION: (1)..(1)
<220> FEATURE:
<221> NAME/KEY: UNSURE
<222> LOCATION: (1)..(1)
<223> OTHER INFORMATION: Unresolved residue
<220> FEATURE:
<221> NAME/KEY: UNSURE
<222> LOCATION: (7)..(7)
<223> OTHER INFORMATION: Unresolved residue
<220> FEATURE:
```

```
<221> NAME/KEY: NON_TER
<222> LOCATION: (10)..(10)

<400> SEQUENCE: 7

Xaa Ile Gly Gly Arg Glu Xaa Leu Lys Asn
1               5                   10

<210> SEQ ID NO 8
<211> LENGTH: 10
<212> TYPE: PRT
<213> ORGANISM: Canis familiaris
<220> FEATURE:
<221> NAME/KEY: NON_TER
<222> LOCATION: (1)..(1)
<220> FEATURE:
<221> NAME/KEY: UNSURE
<222> LOCATION: (3)..(3)
<223> OTHER INFORMATION: Unresolved residue
<220> FEATURE:
<221> NAME/KEY: UNSURE
<222> LOCATION: (10)..(10)
<223> OTHER INFORMATION: Unresolved residue
<220> FEATURE:
<221> NAME/KEY: NON_TER
<222> LOCATION: (10)..(10)

<400> SEQUENCE: 8

Ala Val Xaa Arg Pro Gly Glu Asp Arg Xaa
1               5                   10
```